US 12,210,665 B2

(12) United States Patent
Jarc

(10) Patent No.: US 12,210,665 B2
(45) Date of Patent: Jan. 28, 2025

(54) SYSTEMS AND METHODS FOR FACILITATING OPTIMIZATION OF AN IMAGING DEVICE VIEWPOINT DURING AN OPERATING SESSION OF A COMPUTER-ASSISTED OPERATION SYSTEM

(71) Applicant: Intuitive Surgical Operations, Inc., Sunnyvale, CA (US)

(72) Inventor: Anthony M. Jarc, Johns Creek, GA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 815 days.

(21) Appl. No.: 17/426,368

(22) PCT Filed: Feb. 10, 2020

(86) PCT No.: PCT/US2020/017535
§ 371 (c)(1),
(2) Date: Jul. 28, 2021

(87) PCT Pub. No.: WO2020/167678
PCT Pub. Date: Aug. 20, 2020

(65) Prior Publication Data
US 2022/0096164 A1 Mar. 31, 2022

Related U.S. Application Data

(60) Provisional application No. 62/804,688, filed on Feb. 12, 2019.

(51) Int. Cl.
*A61B 34/20* (2016.01)
*A61B 1/00* (2006.01)
(Continued)

(52) U.S. Cl.
CPC .......... *G06F 3/011* (2013.01); *A61B 1/00042* (2022.02); *A61B 34/20* (2016.02);
(Continued)

(58) Field of Classification Search
CPC ......... G06F 3/011; A61B 34/20; A61B 34/25; A61B 34/35; A61B 90/361;
(Continued)

(56) References Cited

U.S. PATENT DOCUMENTS

2013/0335508 A1   12/2013   Mauchly
2016/0100909 A1   4/2016    Wollowick et al.
(Continued)

FOREIGN PATENT DOCUMENTS

JP   2002510230 A   4/2002
JP   2015228954 A   12/2015
(Continued)

OTHER PUBLICATIONS

International Preliminary Report on Patentability for Application No. PCT/US2020/017535. mailed on Aug. 26, 2021, 11 pages.
(Continued)

*Primary Examiner* — Syed Haider

(57) ABSTRACT

A viewpoint optimization system identifies a condition associated with an operating session during which a computer-assisted operation system performs a plurality of operations with respect to a body while an imaging device included within the computer-assisted operation system provides, for display on a display device during the operating session, imagery of the body from a first viewpoint. The viewpoint optimization system defines, based on the identified condition, a second viewpoint for the imaging device that is more optimal than the first viewpoint for an operation included in the plurality of operations. Additionally, the viewpoint optimization system directs the display device to display an
(Continued)

indication of the second viewpoint. Corresponding systems and methods are also disclosed.

20 Claims, 14 Drawing Sheets

(51) Int. Cl.
    *A61B 34/00*     (2016.01)
    *A61B 34/35*     (2016.01)
    *A61B 90/00*     (2016.01)
    *G06F 3/01*     (2006.01)
    *A61B 17/00*     (2006.01)
    *A61B 34/10*     (2016.01)

(52) U.S. Cl.
    CPC .............. *A61B 34/25* (2016.02); *A61B 34/35* (2016.02); *A61B 90/361* (2016.02); *A61B 2017/00207* (2013.01); *A61B 2034/107* (2016.02); *A61B 2034/2074* (2016.02); *A61B 2090/367* (2016.02)

(58) Field of Classification Search
    CPC .......... A61B 1/00042; A61B 2034/107; A61B 2034/2074; A61B 2017/00207
    See application file for complete search history.

(56) References Cited

U.S. PATENT DOCUMENTS

| | | | |
|---|---|---|---|
| 2017/0027651 A1 | 2/2017 | Esterberg | |
| 2017/0042407 A1* | 2/2017 | Miyai | G16H 30/20 |
| 2017/0046842 A1* | 2/2017 | Yamaguchi | A61B 1/000095 |
| 2017/0189127 A1 | 7/2017 | Weir | |
| 2017/0195615 A1 | 7/2017 | Han et al. | |
| 2017/0245739 A1* | 8/2017 | Yamamura | A61B 1/018 |
| 2018/0296280 A1 | 10/2018 | Kurihara et al. | |
| 2018/0338806 A1 | 11/2018 | Grubbs | |
| 2018/0344412 A1 | 12/2018 | Esterberg | |
| 2019/0015162 A1* | 1/2019 | Abhari | A61B 34/20 |
| 2020/0085282 A1* | 3/2020 | Wada | G02B 21/0012 |

FOREIGN PATENT DOCUMENTS

| | | |
|---|---|---|
| JP | 2018161377 A | 10/2018 |
| JP | 2018531731 A | 11/2018 |
| WO | WO-2007047782 A2 | 4/2007 |
| WO | WO-2015143067 A1 | 9/2015 |
| WO | WO-2016136613 A1 | 9/2016 |
| WO | WO-2016149345 A1 | 9/2016 |
| WO | WO-2018179675 A1 | 10/2018 |
| WO | WO-2018179749 A1 | 10/2018 |
| WO | WO-2019005983 A1 | 1/2019 |

OTHER PUBLICATIONS

International Search Report and Written Opinion for Application No. PCT/US2020/017535, mailed May 13, 2020, 13 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR FACILITATING OPTIMIZATION OF AN IMAGING DEVICE VIEWPOINT DURING AN OPERATING SESSION OF A COMPUTER-ASSISTED OPERATION SYSTEM

RELATED APPLICATIONS

The present application is a U.S. National Stage Application under 35 U.S.C. § 371 of International Application No. PCT/US2020/017535, filed on Feb. 10, 2020, which claims priority to U.S. Provisional Patent Application No. 62/804,688, filed on Feb. 12, 2019, the contents of which are hereby incorporated by reference in their entirety.

BACKGROUND INFORMATION

Various technologies including computing technologies, robotic technologies, medical technologies, and extended reality technologies (e.g., augmented reality technologies, virtual reality technologies, etc.) have made it possible for users such as surgeons to perform, and be trained to perform, various types of operations and procedures. For example, users may perform and be trained to perform minimally-invasive medical procedures such as computer-assisted surgical procedures in clinical settings (e.g., operating on bodies of live human or animal patients), in non-clinical settings (e.g., operating on bodies of human or animal cadavers, bodies of tissue removed from human or animal anatomies, etc.), in training settings (e.g., operating on bodies of physical anatomical training models, bodies of virtual anatomy models in extended reality environments, etc.), and so forth.

During an operating session in any such setting, a user may view imagery of an operational area associated with a body (e.g., an area internal to the body) as the user directs instruments of a computer-assisted operation system to perform operations with respect to the body at the operational area. The imagery may be provided by an imaging device included within the computer-assisted operation system, such as an endoscope. As various operations are performed in this way, a viewpoint of the imaging device may significantly affect how efficiently and effectively the user is able to perform the operations.

SUMMARY

Systems and methods for facilitating optimization of an imaging device viewpoint during an operating session of a computer-assisted operation system are described herein. For instance, one embodiment is implemented as a system comprising a memory storing instructions and a processor communicatively coupled to the memory and configured to execute the instructions. For example, the instructions may direct the processor to identify a condition associated with an operating session during which a computer-assisted operation system performs a plurality of operations with respect to a body while an imaging device included within the computer-assisted operation system provides, for display on a display device during the operating session, imagery of the body from a first viewpoint. The instructions may also direct the processor to define, based on the identified condition, a second viewpoint for the imaging device that is more optimal than the first viewpoint for an operation included in the plurality of operations. Additionally, the instructions may cause the processor to direct the display device to display an indication of the second viewpoint.

Another exemplary embodiment is also implemented as a system comprising a memory storing instructions and a processor communicatively coupled to the memory and configured to execute the instructions. In this embodiment, the instructions may direct the processor to determine, during an operating session in which a computer-assisted operation system performs a plurality of operations with respect to a body while an imaging device included within the computer-assisted operation system provides imagery of the body from a first viewpoint for display to a user by way of a display device, that the user uses a first wrist posture associated with the first viewpoint to direct the computer-assisted operation system to perform an operation included in the plurality of operations. The instructions may also direct the processor to define, during the operating session, a second viewpoint associated with a second wrist posture that is more optimal for directing the performing of the operation than the first wrist posture, the second viewpoint having a horizon orientation distinct from a horizon orientation of the first viewpoint. The instructions may further direct the processor to direct, while the display device is displaying the imagery of the body from the first viewpoint, the display device to integrate, with the displayed imagery of the body from the first viewpoint, a reticle overlay graphic indicative of the horizon orientation of the second viewpoint. In response to the integration of the reticle overlay graphic indicative of the horizon orientation of the second viewpoint, the instructions may direct the processor to receive user input indicating that the user selects to view imagery of the body from the second viewpoint instead of viewing the imagery of the body from the first viewpoint. Accordingly, the instructions may direct the processor to direct the display device to switch, in response to the user input, from displaying the imagery of the body from the first viewpoint to displaying the imagery of the body from the second viewpoint.

Another exemplary embodiment is implemented as a method performed by a viewpoint optimization system. For example, the method includes identifying a condition associated with an operating session during which a computer-assisted operation system performs a plurality of operations with respect to a body while an imaging device included within the computer-assisted operation system provides, for display on a display device during the operating session, imagery of the body from a first viewpoint. The method also includes defining, based on the condition, a second viewpoint for the imaging device that is more optimal than the first viewpoint for an operation included in the plurality of operations. Additionally, the method includes directing the display device to display an indication of the second viewpoint.

Another exemplary embodiment is implemented by a non-transitory, computer-readable medium storing instructions that, when executed, direct a processor of a computing device to perform operations described herein. For example, the instructions may direct the processor to identify a condition associated with an operating session during which a computer-assisted operation system performs a plurality of operations with respect to a body while an imaging device included within the computer-assisted operation system provides, for display on a display device during the operating session, imagery of the body from a first viewpoint. The instructions may also direct the processor to define, based on the identified condition, a second viewpoint for the imaging device that is more optimal than the first viewpoint for an operation included in the plurality of operations. Additionally, the instructions may cause the processor to direct the display device to display an indication of the second viewpoint.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
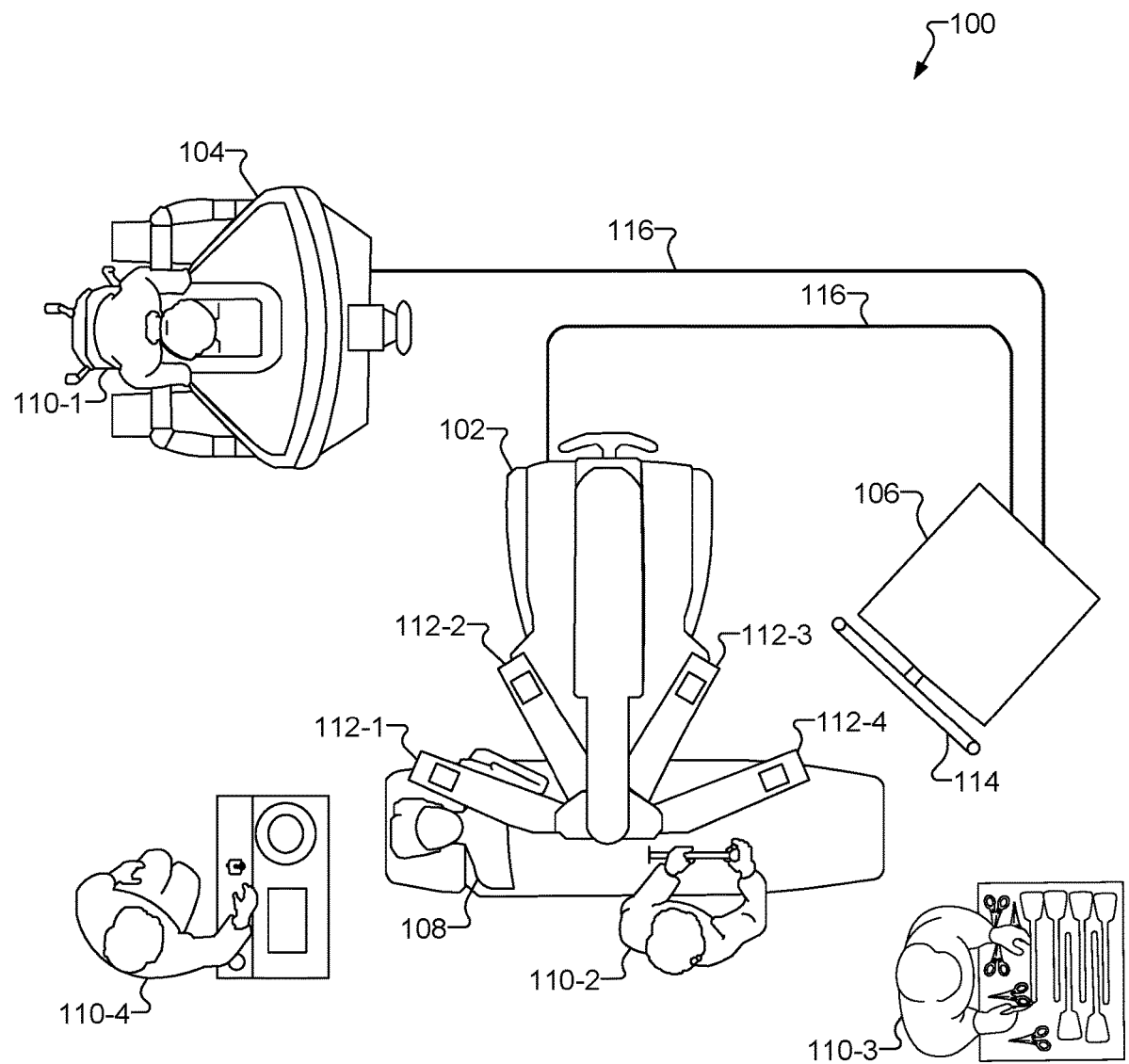
FIG. 1 illustrates an exemplary computer-assisted operation system according to principles described herein.

Systems and methods for facilitating optimization of an imaging device viewpoint during an operating session of a computer-assisted operation system are described herein. As mentioned above, the effectiveness and efficiency with which a user (e.g., a surgeon, a member of a surgical team, another user of a computer-assisted operation system, etc.) may be able to direct a computer-assisted operation system (e.g., a computer-assisted surgical system) to perform a particular operation may be significantly affected by a viewpoint of an imaging device capturing and providing imagery that is displayed for the user during the performance of the operation. Unfortunately, however, consistent and effective optimization of imaging device viewpoints may be a difficult skill for users to master as they become accustomed to using computer-assisted operation systems. Additionally, in certain scenarios (e.g., training scenarios, operating scenarios in accordance with preferences of certain users, operations performed using conventional laparoscopic techniques, etc.), it may be undesirable for the skill of viewpoint optimization to come into play at all. For example, in these scenarios, it may be desirable for optimization of imaging device viewpoints to be performed in a fully automated manner to allow users to focus on other aspects of the operation other than viewpoint optimization. Accordingly, systems and methods described herein may be configured to facilitate users (including novice computer-assisted operation system users undergoing training to learn to use the systems) in improving their viewpoint selection performance and skills. As will be described below, this is done by making it easier for users to see, understand, and switch to more optimal views during clinical, non-clinical, training, or other operating sessions. For example, systems and methods described herein may facilitate optimization of viewpoints in real time during an operating session by making recommendations to encourage the user to switch viewpoints, semi-automatically switching the viewpoint, automatically switching the viewpoint, or the like.

In one exemplary implementation, a system for facilitating optimization of an imaging device viewpoint may include or be implemented by a memory storing instructions and a processor communicatively coupled to the memory and configured to execute the instructions to perform functionality associated with facilitating the optimization of a viewpoint from which an imaging device captures and provides imagery during an operating session. For example, in accordance with the instructions, the system may identify a condition associated with an operating session during which a computer-assisted operation system performs a plurality of operations with respect to a body while an imaging device included within the computer-assisted operation system provides, for display on a display device during the operating session, imagery of the body from a first viewpoint. For example, as will be described in more detail below, the identified condition may relate to a current wrist posture of the user, a specific operation included in the plurality of operations being performed, the identity of the user directing the computer-assisted operation system to perform the operation, known habits of the identified user (e.g., previously observed performance strengths and weaknesses, etc.), current cartesian positions of the user's hands with respect to one another, a co-location status of the user's hands with respect to instruments being controlled, or the like.

Based on the identified condition, the system may define a second viewpoint for the imaging device that is more optimal than the first viewpoint for the operation being performed and may direct the display device to display an indication of the second viewpoint. For example, as will be described in more detail below, the system may direct the display device to display the indication of the second viewpoint by automatically or semi-automatically switching from displaying imagery captured from the first viewpoint to imagery captured from the second viewpoint. As another example, the system may direct the display device to display the indication of the second viewpoint by directing the display device to continue displaying the imagery captured from the first viewpoint while also introducing a graphical overlay or other indicator that is presented together with (e.g., integrated with) the imagery being presented from the first viewpoint.

As used herein, "optimization" of a viewpoint may refer to an altering of one or more characteristics (e.g., one or more aspects or parameters defining an orientation) of the viewpoint in order to improve the viewpoint for a particular operation. As such, a viewpoint that is "more optimal" for a particular operation than another viewpoint will be understood to be improved in some way (e.g., so as to make the operation easier to perform effectively and/or efficiently), but it will also be understood that an "optimized" viewpoint or a "more optimal" viewpoint may not necessarily be the most optimal viewpoint possible for the operation. A determination that a viewpoint is more optimal than another viewpoint may be subjective (e.g., based on an opinion of an experienced user, etc.) or objective (e.g., based on a viewpoint selection algorithm, etc.).

Implementations of the systems and methods described herein generally relate to or employ computer-assisted operation systems such as computer-assisted medical systems (e.g., minimally-invasive robotic surgery systems, conventional laparoscopic surgical systems that employ robotic endoscopes or other computer-assisted vision systems, etc.). As will be described in more detail below, however, it will be understood that inventive aspects disclosed herein may be embodied and implemented in various ways, including by employing robotic and non-robotic embodiments and implementations. Implementations relating to surgical or other medical systems are merely exemplary and are not to be considered as limiting the scope of the inventive aspects disclosed herein. For example, any reference to surgical instruments, surgical techniques, and/or other such details relating to a surgical context will be understood to be non-limiting as the instruments, systems, and methods described herein may be used for medical treatment or diagnosis, cosmetic improvements, imaging of human or animal anatomy, gathering data from human or animal anatomy, setting up or taking down systems, training medical or non-medical personnel, and so forth (any of which may or may not also involve surgical aspects). In other examples, the instruments, systems, and methods described herein may also be used for procedures performed on, or with, animals, human cadavers, animal cadavers, portions of human or animal anatomy, tissue removed from human or animal anatomies (which may or may not be re-implanted within the human or animal anatomy), non-tissue work pieces, training models, and so forth. In yet other examples, the instruments, systems, and methods described herein may be applied for non-medical purposes including for industrial systems, general robotics, teleoperational systems, and/or sensing or manipulating non-tissue work pieces.

Various benefits may be provided by the systems and methods described herein for facilitating optimization of imaging device viewpoints. In non-computer-assisted operating sessions (e.g., standard surgical procedures that do not employ robotic or other computer-assisted operating technology), it may be intuitive and natural for a surgeon to move his or her head and body to achieve an optimal viewpoint of the body being operated on, as well as to find a good angle to perform various operations. For instance, if a surgeon needs to see more detail, he or she may naturally move his or her head closer to the operating area to get a better look. As another example, a certain wrist posture may provide the most comfort and control for performing an operation such as suturing an incision to close it off, and, as such, it may be natural for the surgeon to position himself or herself with respect to the body to be able to use that wrist posture as he or she performs the suturing operation.

When directing a computer-assisted operation system to perform similar operations, the same principles (e.g., of viewing angle and detail, of wrist posture, etc.) may apply, but it may be less intuitive for users, particularly users new to computer-assisted operation systems, to successfully achieve optimal viewpoints (e.g., viewpoints that provide optimal views of an operating area, viewpoints that are associated with optimal wrist postures, etc.). For example, a surgeon who may wish to see a more detailed view of an operating area while performing an operation using a computer-assisted operation system may not be able to simply move his or her head closer to the patient to get a better view. Rather, to achieve a more optimal viewpoint, the surgeon may have to perform a more deliberate series of actions. For example, the surgeon may press a foot pedal to switch the system from an operating mode in which robotic instruments follow or mimic the surgeon's hand movements to an imaging adjustment mode in which the surgeon uses hand gestures to modify the orientation of the imaging device (e.g., to zoom, pan, rotate, and/or articulate the imaging device, etc.). The surgeon may make imaging device orientation adjustments in the imaging adjustment mode and then may reposition his or her hands and perform certain additional actions (e.g., a pinch action or the like) to switch the computer-assisted operation system back into the operating mode.

While expert users may be very adept at this process so as to comfortably make imaging adjustments as often as every second or every few seconds during an operating session, less experienced users may be less comfortable with these imaging adjusting procedures. As a result, these users may be less likely to switch from one viewpoint to another, even if the new viewpoint would be more optimal. Additionally, less experienced users may not be fully cognizant of the extent to which a selected viewpoint not only determines what can been seen, but also the wrist posture that may be used, the sensitivity of hand movements that may be used, and so forth. As such, these users may inadvertently or unknowingly use suboptimal wrist postures or otherwise fail to take full advantage of benefits associated with an optimal viewpoint. As a result, various operations performed by these users may be more difficult and/or time consuming to perform than they could be if a more optimal viewpoint were used.

To remedy these challenges, systems and methods described herein help train and direct users (e.g., surgeons, etc.) to find more optimal viewpoints, to more successfully use viewpoints to increase the efficiency and/or effectiveness of operations being performed, and so forth. As will be described in more detail below, the systems and methods described herein may be used during clinical operating sessions as well as to help provide training and practice during non-clinical or training operating sessions. Additionally, the systems and methods described herein may make it easier to switch from a less optimal viewpoint to a more optimal viewpoint, such that even experienced users of computer-assisted operation systems (e.g., expert users who are already adept at finding optimal viewpoints) may benefit from the facilitated viewpoint switching as they constantly and consistently update their viewpoints to remain optimal during an operating session. Accordingly, for both novice and expert users, the systems and methods described herein may ultimately help lead to easier, more effective, and more efficient performance of operations; decreased learning curves on complex computer-assisted operation systems; and, in the case of medically-related systems, improved outcomes for patients.

Various embodiments will now be described in more detail with reference to the figures. The systems and methods described herein may provide one or more of the benefits mentioned above as well as various additional and/or alternative benefits that will be made apparent by the description below.

Viewpoint optimization systems and methods described herein may operate as part of or in conjunction with a computer-assisted operation system (e.g., a computer-assisted medical system such as a robotic surgical system). As such, in order to promote an understanding of viewpoint optimization systems and methods described herein, an exemplary computer-assisted operation system will now be described. The described exemplary computer-assisted operation system is illustrative and not limiting. Viewpoint optimization systems and methods described herein may be integrated with (e.g., built into) or otherwise operate as part of or in conjunction with the computer-assisted operation systems described herein and/or other suitable computer-assisted operation systems.

FIG. 1 illustrates an exemplary computer-assisted operation system 100 ("operation system 100"). While, as mentioned above, computer-assisted operation systems may be used to perform various types of operations in various types of applications, operation system 100 will be understood to be a computer-assisted medical system configured for use in performing operations related to surgical and/or non-surgical medical procedures. As shown, operation system 100 may include a manipulating system 102, a user control system 104, and an auxiliary system 106 communicatively coupled one to another. Operation system 100 may be utilized by a medical team to perform a computer-assisted medical procedure or other such procedure on a body of a patient 108 or any other body as may serve a particular implementation. As shown, the medical team may include a first clinician 110-1 (e.g., a surgeon or other physician), an assistant 110-2, a nurse 110-3, and a second clinician 110-4 (e.g., an anesthesiologist or other physician), all of whom may be collectively referred to as "team members 110," and each of whom may control, interact with, or otherwise be a user of operation system 100. Additional, fewer, or alternative team members may be present during a medical procedure as may serve a particular implementation. For example, for some medical procedures, the "clinician 110-1" may not be a medical doctor. Further, team composition for non-medical procedures generally differ, and include other combinations of members serving non-medical roles.

While FIG. 1 illustrates an ongoing medical procedure such as a minimally invasive surgical procedure, it will be understood that operation system 100 may similarly be used to perform open surgical procedures or other types of operations that may similarly benefit from the accuracy and convenience of operation system 100. For example, operations such as exploratory imaging operations, mock medical procedures used for training purposes, and/or other operations may also be performed using operation system 100. Additionally, it will be understood that any medical procedure or other operation for which operation system 100 is employed may not only include an operative phase, but may also include preoperative, postoperative, and/or other such operative phases.

As shown in FIG. 1, manipulating system 102 may include a plurality of manipulator arms 112 (e.g., manipulator arms 112-1 through 112-4) to which a plurality of instruments (e.g., surgical instruments, other medical instruments, or other instruments, etc.) may be coupled. Each instrument may be implemented by any suitable surgical tool (e.g., a tool having tissue-interaction functions), medical tool, imaging device (e.g., an endoscope), sensing instrument (e.g., a force-sensing instrument), diagnostic instrument, or the like that may be used for a computer-assisted medical procedure such as a surgical procedure on patient 108 (e.g., by being at least partially inserted into patient 108 and manipulated to perform a computer-assisted medical procedure on patient 108). While manipulating system 102 is depicted and described herein as including four manipulator arms 112, it will be recognized that manipulating system 102 may include only a single manipulator arm 112 or any other number of manipulator arms as may serve a particular implementation. Additionally, it will be understood that, in some exemplary systems, certain instruments may not be coupled to or controlled by manipulator arms, but rather may be handheld and controlled manually (e.g., by a surgeon, other clinician, or other medical personnel). For instance, certain handheld devices of this type may be used in conjunction with or as an alternative to computer-assisted instrumentation that is coupled to manipulator arms 112 shown in FIG. 1 and is described in various examples herein.

Manipulator arms 112 and/or instruments attached to manipulator arms 112 may include one or more displacement transducers, orientational sensors, and/or positional sensors used to generate raw (i.e., uncorrected) kinematics information, One or more components of operation system 100 may be configured to use the kinematics information to track (e.g., determine positions of) and/or control the instruments.

User control system 104 may be configured to facilitate control by clinician 110-1 of manipulator arms 112 and instruments attached to manipulator arms 112. For a surgical procedure, for example, clinician 110-1 may be a surgeon. In this example, clinician 110-1 may interact with user control system 104 to remotely move or manipulate manipulator arms 112 and the instruments to perform a plurality of operations included within a surgical or other medical procedure. To this end, user control system 104 may provide clinician 110-1 with imagery (e.g., high-definition 3D imagery) of the body of patient 108 captured from a particular viewpoint by an imaging device. In certain examples, user control system 104 may include a stereo viewer having two displays where stereoscopic imagery of the body captured from the viewpoint by a stereoscopic imaging device may be viewed by clinician 110-1. Clinician 110-1 may utilize the imagery to perform one or more procedures with one or more instruments attached to manipulator arms 112.

To facilitate control of instruments, user control system 104 may include a set of master controls. These master controls may be manipulated by clinician 110-1 to control movement of instruments (e.g., by utilizing robotic and/or teleoperation technology). The master controls may be configured to detect a wide variety of hand, wrist, and finger movements by clinician 110-1. In this manner, clinician 110-1 may intuitively perform a procedure using one or more instruments. As mentioned above, the master controls, as well as other controls such as foot pedals and so forth, may allow clinician 110-1 not only to control manipulator arms 112 to perform the operations required for the surgical procedure, but also to control at least one manipulator arm 112 associated with an imaging device so as to set and continually adjust the orientation (e.g., the zoom, horizon, planar, pitch, yaw, and/or other aspects of the orientation) of the imaging device as the operations are performed.

Auxiliary system 106 may include one or more computing devices configured to perform primary processing operations of operation system 100. In such configurations, the one or more computing devices included in auxiliary system 106 may control and/or coordinate operations performed by various other components of operation system 100 such as manipulating system 102 and/or user control system 104. For example, a computing device included in user control system 104 may transmit instructions to manipulating system 102 by way of the one or more computing devices included in auxiliary system 106. As another example, auxiliary system 106 may receive and process image data representative of imagery captured by an imaging device attached to one of manipulator arms 112.

In some examples, auxiliary system 106 may be configured to present visual content to team members 110 who may not have other access to the images provided to clinician 110-1 at user control system 104. To this end, auxiliary system 106 may include a display monitor 114 configured to display one or more user interfaces, imagery (e.g., 2D or 3D imagery) of the body of patient 108, information associated with patient 108 and/or the medical procedure, and/or any other content as may serve a particular implementation. In some examples, display monitor 114 may display imagery of the body together with additional content (e.g., graphical content, contextual information, etc.) concurrently displayed with the images. Display monitor 114 may be implemented by a touchscreen display with which team members 110 may interact (e.g., by way of touch gestures) to provide user input to operation system 100, or may be implemented by any other type of display screen as may serve a particular implementation.

As will be described in more detail below, a viewpoint optimization system may be implemented within or may operate in conjunction with operation system 100. For instance, in certain implementations, a viewpoint optimization system may be implemented by user control system 104 (e.g., using a display device such as the stereoscopic viewer included within user control system 104), auxiliary system 106 (e.g., using a display device such as display monitor 114) or by another suitable device.

Manipulating system 102, user control system 104, and auxiliary system 106 may be communicatively coupled one to another in any suitable manner. For example, as shown in FIG. 1, manipulating system 102, user control system 104, and auxiliary system 106 may be communicatively coupled by way of control lines 116, which may represent any wired or wireless communication link as may serve a particular implementation. To this end, manipulating system 102, user control system 104, and auxiliary system 106 may each include one or more wired or wireless communication interfaces, such as one or more local area network interfaces, Wi-Fi network interfaces, cellular interfaces, etc.

Figure 2:
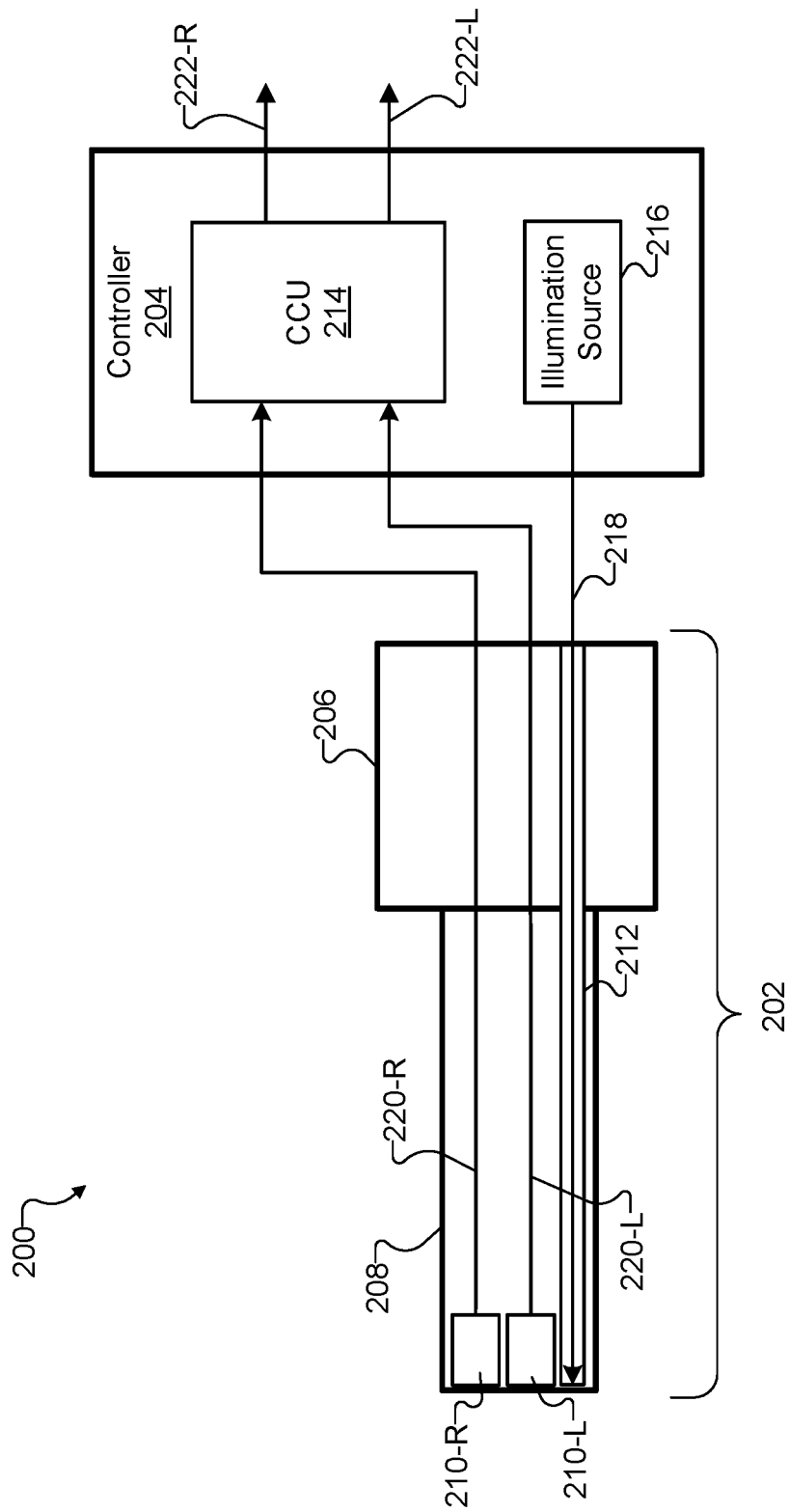
FIG. 2 illustrates an exemplary imaging device included within the computer-assisted operation system of FIG. 1 according to principles described herein.

FIG. 2 illustrates an exemplary imaging system 200 that may be used in accordance with the systems and methods described herein to capture imagery of a body from various viewpoints characterized by various aspects of orientation as will be described below. As shown, imaging system 200 includes an imaging device 202 and a controller 204. Imaging system 200 may include additional or alternative components as may serve a particular implementation. For example, imaging system 200 may include various optical and/or electrical signal transmission components (e.g., wires, lenses, optical fibers, choke circuits, waveguides, etc.), a cable that houses electrical wires and/or optical fibers and that is configured to interconnect imaging device 202 and controller 204, or the like.

Imaging device 202 may be implemented by an endoscope or similar such imaging tool (e.g., a laparoscope, etc.) configured to capture imagery of a scene such as an internal view of any of the bodies described herein. In the example of FIG. 2, imaging device 202 is stereoscopic. In other examples, however, imaging device 202 may be monoscopic (e.g., by including one image sensor instead of two image sensors). Additionally, while imaging devices such as endoscopes, laparoscopes, and so forth may capture imagery of a body in the manner described herein in relation to FIG. 2, it will be understood that other imaging technologies (e.g., ultrasound imaging, imaging outside of the visible light range, etc.) and other types of imaging devices or combinations of devices may be used to capture the imagery of the body in other examples.

For instance, ultrasound imaging or other such technologies may be employed in certain examples in which an imaging device includes an ultrasound probe that is inserted into an operational area and may be manipulated using instruments attached to manipulator arms, rather than being controlled by itself being directly attached to a manipulator arm. As another example, hyperspectral imaging technologies and tools may be used to capture images in other regions of the electromagnetic spectrum other than the visible light spectrum. This may facilitate, for example, imaging of features (e.g., blood vessels, etc.) that may be underneath an outer surface that reflects visible light. Similarly, performing infrared, ultraviolet, or other hyperspectral imaging may allow for imaging techniques in which fluorescent imaging agents are injected into tissue to highlight different features at different times due to known metabolization and/or decomposition patterns of the imaging agents. Such imaging technologies may be implemented by different modalities supported by a single imaging system (e.g., imaging system 200) or by different imaging systems (e.g., an imaging system that may be swapped in for imaging system 200 if desired by the medical team performing the operation).

As shown, imaging device 202 includes a camera head 206, a shaft 208 coupled to and extending away from camera head 206, image sensors 210 (i.e., a right-side image sensor 210-R and a left-side image sensor 210-L) at a distal end of shaft 208, and an illumination channel 212. Each of these elements will now be described in more detail.

In some examples, imaging device 202 may be controlled by way of computer and/or robotic assistance by a surgical team member such as clinician 110-1. For instance, camera head 206 may be coupled to a manipulator arm of a computer-assisted operation system (e.g., one of manipulator arms 112 of operation system 100) and controlled using robotic and/or teleoperation technology.

The distal end of shaft 208 may be positioned at an operational area that is to be imaged by imaging device 202. In this configuration, imaging device 202 may be used to capture imagery of anatomy and/or other objects that are part of a body or are in the vicinity of the body. In various implementations, shaft 208 is rigid (as shown in FIG. 2). Alternatively, shaft 208 may be jointed (e.g., including an articulation mechanism to allow for pitch and/or yaw orientation adjustments) and/or may be flexible. Additionally, while the distal end of shaft 208 is shown in this example to terminate at an orthogonal angle in relation to the axis of shaft 208 such that imaging device 202 captures imagery of objects around the axis of shaft 208 (i.e., objects that are straight ahead), in other examples, the distal end of shaft 208 may be tapered at an angle (e.g., a 30° angle, a 45° angle, etc.) that is non-orthogonal to the axis of shaft 208. In this way, imaging device 202 may capture imagery of objects that are offset from the axis of shaft 208, thereby allowing for more flexibility in where a field of view of imaging device 202 may be directed.

Image sensors 210 may each be implemented by any suitable image sensor, such as a charge coupled device ("CCD") image sensor, a complementary metal-oxide semiconductor ("CMOS") image sensor, or the like. In some examples, as shown in FIG. 2, image sensors 210 are positioned at the distal end of shaft 208. Alternatively, image sensors 210 may be positioned closer to a proximal end of shaft 208, inside camera head 206, or outside imaging device 202 (e.g., inside controller 204). In these alternative configurations, optics (e.g., lenses, optical fibers, etc.) included in shaft 208 and/or camera head 206 may convey light from a scene to image sensors 210.

Image sensors 210 are configured to detect (e.g., capture, collect, sense, or otherwise acquire) light. For example, image sensor 210-R is configured to detect the light from a right-side perspective, and image sensor 210-L is configured to detect the light from a left-side perspective. The light detected by image sensors 210 may include, for example, visible light reflecting off the body or objects located within the field of view, hyperspectral (i.e., non-visible) light reflecting off the body, fluorescence illumination generated by a fluorescence imaging agent in the body, or any other light having any frequency as may serve a particular implementation. As described in more detail below, image sensors 210 may convert the detected light into data representative of one or more images.

Illumination channel 212 may be implemented by one or more optical components (e.g., optical fibers, light guides, lenses, etc.). As will be described below, illumination may be provided by way of illumination channel 212 to illuminate the operational area and the objects included therein.

Controller 204 may be implemented by any suitable combination of hardware and software configured to control and/or interface with imaging device 202. For example, controller 204 may be at least partially implemented by a computing device included in auxiliary system 106.

Controller 204 includes a camera control unit ("CCU") 214 and an illumination source 216. Controller 204 may include additional or alternative components as may serve a particular implementation. For example, controller 204 may include circuitry configured to provide power to components included in imaging device 202. In some examples, CCU 214 and/or illumination source 216 are alternatively included in imaging device 202 (e.g., in camera head 206).

CCU 214 is configured to control various parameters (e.g., activation times, auto exposure, etc.) of image sensors 210. As will be described below, CCU 214 may be further configured to receive and process image data from image sensors 210. While CCU 214 is shown in FIG. 2 to be a single unit, CCU 214 may alternatively be implemented by a first CCU configured to control right-side image sensor 210-R and a second CCU configured to control left-side image sensor 210-L.

Illumination source 216 may be configured to generate and emit illumination 218. Illumination 218 (which is also referred herein to as light) may travel by way of illumination channel 212 to a distal end of shaft 208, where illumination 218 exits to illuminate a scene.

Illumination 218 may include visible or hyperspectral light having one or more frequency (e.g., color) components. Illumination 218 may additionally or alternatively include fluorescence excitation illumination configured to elicit fluorescence illumination by a fluorescence imaging agent (e.g., by exciting a fluorescence imaging agent that has been injected into a bloodstream of a patient to begin emitting fluorescence illumination). In some examples, the fluorescence excitation illumination has a wavelength in an infrared light region (e.g., in a near-infrared light region). While a single illumination source 216 is shown to be included in controller 204, multiple illumination sources each configured to generate and emit differently configured illumination may alternatively be included in controller 204.

To capture one or more images of a scene, controller 204 (or any other suitable computing device) may activate illumination source 216 and image sensors 210. While activated, illumination source 216 emits illumination 218, which travels via illumination channel 212 to the operational area. Image sensors 210 detect illumination 218 reflected from one or more surfaces of anatomy of the body or other objects in the vicinity of the body. In cases where illumination 218 includes fluorescence excitation illumination, image sensors 210 may additionally or alternatively detect fluorescence illumination that is elicited by the fluorescence excitation illumination.

Image sensors 210 (and/or other circuitry included in imaging device 202) may convert the sensed light into image data 220 representative of one or more images of the scene. For example, image sensor 210-R outputs image data 220-R representative of images captured from a right-side perspective and image sensor 210-L outputs image data 220-L representative of images captured from a left-side perspective. Image data 220 may have any suitable format and may be transmitted from image sensors 210 to CCU 214 in any suitable way.

CCU 214 may process (e.g., packetize, format, encode, etc.) image data 220 and output processed image data 222 (e.g., processed image data 222-R corresponding to image data 220-R and processed image data 222-L corresponding to image data 220-14. Processed image data 222 may be transmitted to an image processor (not shown), which may prepare processed image data 222 for display on one or more display devices (e.g., in the form of a video stream and/or one or more still images). For example, the image processor may, based on image data 222, generate one or more full color images, grayscale images, and/or fluorescence images for display on one or more display devices such as the stereoscopic viewer of user control system 104 or display monitor 114 of auxiliary system 106.

As imaging system 200 captures imagery of a body in the ways described above, imaging system may capture the imagery from a particular viewpoint. Based on user preference, which operation is being performed at any given time, and various other factors, it may be desirable for the viewpoint from which the imagery is captured to be adjusted by adjusting one or more aspects of an orientation of the viewpoint.

Figure 3:
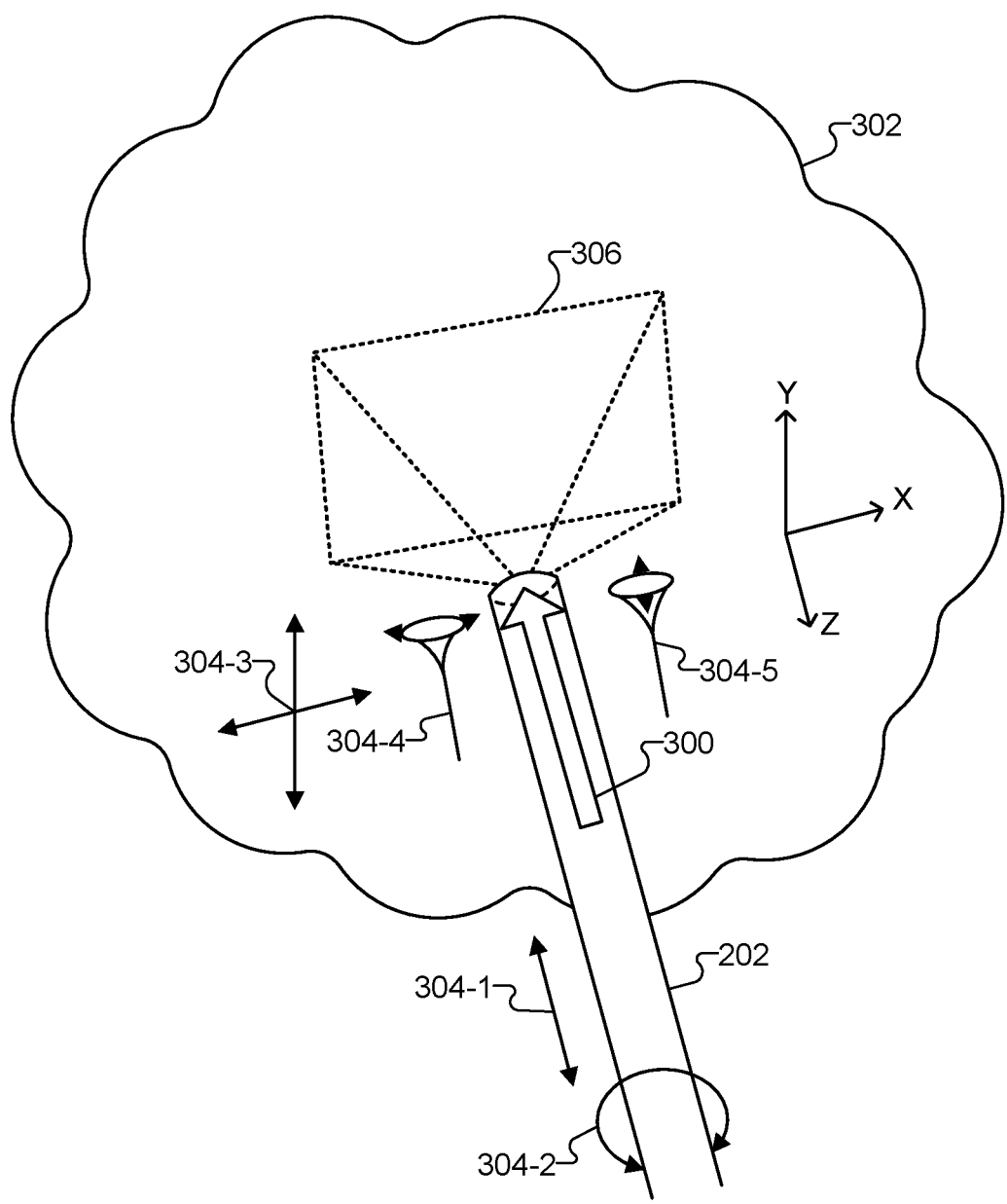
FIG. 3 illustrates an exemplary viewpoint from which an imaging device captures imagery of a body according to principles described herein.

To illustrate, FIG. 3 shows an exemplary viewpoint 300 from which imaging device 202 (within image system 200) captures imagery of a body 302. As mentioned above, operations within an operating session may be performed with respect to (e.g., within) various types of bodies including, but not limited to, a body of a live human patient, a body of a cadaver, a body of a non-human subject (e.g., an animal or the like), or another such biological body. In some examples, the body upon or within which the operation is performed may be only an anatomical portion of one of these other types of bodies. For example, the body may be a disembodied organ or other body part taken from a full biological body, an artificial training fixture (e.g., an artificial organ or other body part), or a virtual body used for training, experimental, and/or other such purposes (e.g., using real or extended reality training systems). In still other examples, a computer-assisted operation system similar to operation system 100 may be useful for performing inspection or repair operations within bodies of complex electrical or mechanical systems such as engines or other complex systems. As yet another example, a computer-assisted operation system may be used in law enforcement or surveillance contexts (e.g., to inspect and disable dangerous explosive devices, to conduct surveillance in tight spaces, etc.), and/or in any other contexts or with any other technologies as may serve a particular implementation.

As used herein, a "viewpoint" of an imaging device (also referred to as an "imaging device viewpoint") such as viewpoint 300 may refer to a combination of various aspects of position, orientation, configuration, resolution, and the like that together combine to define what imagery the imaging device captures at a particular moment in time. FIG. 3 depicts viewpoint 300 as an arrow stretching along the shaft of imaging device 202 to suggest that, as alterations are made to the position, orientation, configuration, resolution, etc., of imaging device 202, viewpoint 300 will be adjusted accordingly.

Viewpoint 300 may be defined by various aspects of position, orientation, configuration, resolution, and so forth of imaging device 202. As will now be described, each of these aspects will be referred to herein as different aspects of an orientation or as different types of orientations 304 (e.g., orientations 304-1 through 304-5) of viewpoint 300.

As shown, a zoom orientation 304-1 of viewpoint 300 relates to an apparent position of viewpoint 300 along the longitudinal axis of the shaft of imaging device 202. Thus, for example, an adjustment in zoom orientation 304-1 may result in imagery that looks larger (closer) or smaller (farther away) as compared to an initial zoom orientation 304-1 that has not been adjusted. In certain implementations, adjustments to zoom orientation 304-1 may be made by physically moving or sliding imaging device 202 closer to the portion of body 302 that is being captured or farther from the portion of body 302 that is being captured. Such zoom adjustments may be referred to herein as optical zoom adjustments. In other implementations, adjustments may be made without physically moving or adjusting the physical orientation of imaging device 202. For example, zoom adjustments may be made optically by internally changing a lens, lens configuration, or other optical aspect of imaging device 202, or by applying a digital zoom manipulation to the image data captured by imaging device 202.

A horizon orientation 304-2 of viewpoint 300 relates to a rotation of imaging device 202 along the longitudinal axis of the shaft of imaging device 202 (i.e., the z-axis according to the coordinate system illustrated in FIG. 3). Thus, for example, an adjustment of 180° in horizon orientation 304-1 would result in imagery that is upside down as compared to a horizon orientation of 0°. In certain implementations, adjustments to horizon orientation 304-1 may be made by physically rotating imaging device 202, while, in other implementations, such adjustments may be made without physically moving or adjusting the physical orientation of imaging device 202. For example, horizon adjustments may be made by digitally manipulating or processing the image data captured by imaging device 202.

A planar orientation 304-3 of viewpoint 300 relates to a position of imaging device with respect to a plane of body 302 that is being captured. As such, planar orientation 304-3 may be adjusted by panning imaging device 202 left, right, up, or down orthogonally to the longitudinal axis (i.e., parallel to the x-y plane according to the coordinate system shown in FIG. 3), When planar orientation 304-3 is adjusted, the imagery of the body scrolls so that a different part of the body is depicted by the image data after the adjustment to planar orientation 304-3 is made than before.

As mentioned above, certain implementations of imaging device 202 may be jointed, flexible, or may otherwise have an ability to articulate to capture imagery in directions away from the longitudinal axis of imaging device 202. Additionally, even if a particular implementation of imaging device 202 is rigid and straight, settings for angled views (e.g., 30° angled views up or down, etc.) may be available to similarly allow the imaging device to capture imagery in directions other than straight ahead. Accordingly, for any of these implementations of imaging device 202, a yaw orientation 304-4 that affects the heading of the imaging device along a normal axis (i.e., the y-axis of the coordinate system shown), as well as a pitch orientation 304-5 that affects the tilt of the imaging device along a transverse axis (i.e., the x-axis of the coordinate system shown) may also be adjustable.

While various orientations 304 have been explicitly described, it will be understood that various other aspects of how imaging device 202 captures imagery of body 302 may similarly be included as adjustable aspects of the orientation of imaging device 202 in certain implementations.

Based on viewpoint 300, imaging device 202 is shown to capture a particular field of view 306 of body 302. It will be understood that field of view 306 may change in various ways (e.g., move side to side, get larger or smaller, etc.) as various orientations 304 of viewpoint 300 of imaging device 202 are adjusted.

Figure 4:
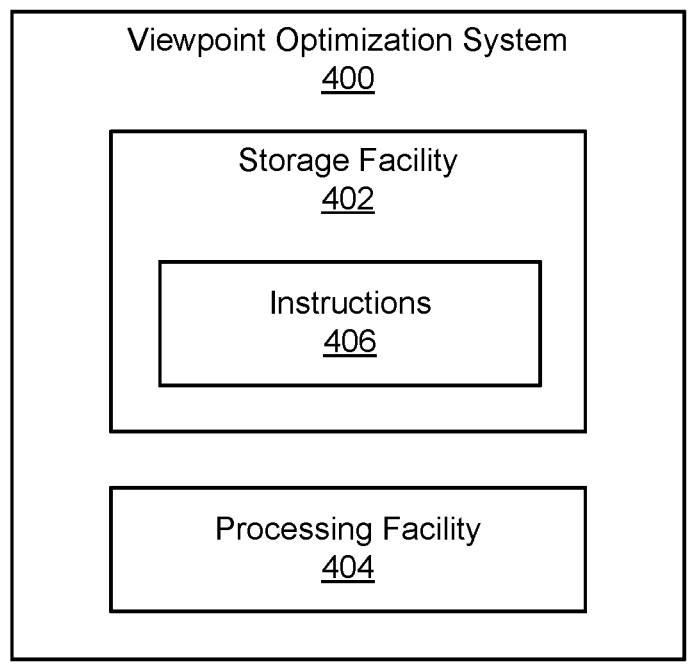
FIG. 4 illustrates an exemplary viewpoint optimization system for facilitating optimization of an imaging device viewpoint during an operating session of a computer-assisted operation system according to principles described herein.

FIG. 4 illustrates an exemplary viewpoint optimization system 400 ("system 400") for facilitating optimization of an imaging device viewpoint (e.g., viewpoint 300 of imaging device 202) during an operating session of a computer-assisted operation system (e.g., operation system 100). As shown in FIG. 4, system 400 may include, without limitation, a storage facility 402 and a processing facility 404 selectively and communicatively coupled to one another. Facilities 402 and 404 may each include or be implemented by hardware and/or software components (e.g., processors, memories, communication interfaces, instructions stored in memory for execution by the processors, etc.). In some examples, facilities 402 and 404 may be distributed between multiple devices and/or multiple locations as may serve a particular implementation.

As mentioned above, system 400 may be implemented by, integrated with, or incorporated into operation system 100

(e.g., by being integrated with auxiliary system 106, user control system 104, etc.) in certain implementations. In other implementations, system 400 may be incorporated into a computing device separate from (but communicatively coupled to) operation system 100. Each of facilities 402 and 404 will now be described in more detail.

Storage facility 402 may maintain (e.g., store) executable data used by processing facility 404 to perform any of the functionality described herein. For example, storage facility 402 may store instructions 406 that may be executed by processing facility 404 to perform any of the functionality described herein. Instructions 406 may be implemented by any suitable application, software, code, and/or other executable data instance. Storage facility 402 may also maintain any data received, generated, managed, used, and/or transmitted by processing facility 404.

Processing facility 404 may be configured to perform (e.g., execute instructions 406 stored in storage facility 402 to perform) various processing functions associated with optimizing (or facilitating optimization of) an imaging device viewpoint during an operating session of a computer-assisted operation system. As used herein, an operating session may refer to any session during which a user (e.g., clinician 110-1) directs a computer-assisted operation system (e.g., operation system 100) to perform one or more operations on any of the types of bodies described herein. For instance, certain operating sessions may be clinical sessions involving surgical procedures performed on human or animal patients, imaging or exploratory procedures performed prior or subsequent to such surgical procedures, or the like. In other examples, operating session may be non-clinical sessions involving training procedures performed on cadaver or artificial bodies, or involving an extended reality (e.g., virtual or augmented reality) body within an extended reality environment.

Processing facility 404 may facilitate optimization of an imaging device viewpoint in any suitable manner. For instance, in one example, processing facility 404 may identify a condition associated with an operating session during which operation system 100 performs a plurality of operations with respect to a body while imaging device 202 (which may be included within operation system 100) provides imagery for display on a display device during the operating session. For example, the imaging device may provide the imagery of the body from a first viewpoint. As will be described in more detail below, the identified condition may be any suitable condition related to a user directing operation system 100 to perform the plurality of operations, the operations themselves, or the like. Based on the identified condition, processing facility 404 may define a second viewpoint for the imaging device that is distinct from the first viewpoint. In particular, the second viewpoint may be defined to be more optimal than the first viewpoint for an operation included in the plurality of operations. Processing facility 404 may then direct the display device to display an indication of the second viewpoint in any of the ways described herein.

As another, more specific example, processing facility 404 may determine, during an operating session such as described in the example above, that the user uses a first wrist posture associated with the first viewpoint to direct the computer-assisted operation system to perform an operation included in the plurality of operations. For instance, processing facility 404 may determine that the user is using a suboptimal wrist posture to perform an operation such as driving a needle through tissue to implement a suture. Processing facility 404 may define a second viewpoint associated with a second wrist posture that is more optimal for directing the performing of the operation than the first wrist posture. For example, processing facility 404 may define the second viewpoint to be associated with a wrist posture that is more neutral (e.g., requiring a less awkward bending or reaching of the user's wrist) for the particular direction that the needle is to be driven through the tissue. The second viewpoint may be defined in any suitable way such as, for example, to have a horizon orientation that is distinct from a horizon orientation of the first viewpoint (e.g., so as to achieve the more neutral wrist posture).

While the display device is displaying the imagery of the body from the first viewpoint, processing facility 404 may direct the display device to integrate, with the displayed imagery of the body from the first viewpoint, a reticle overlay graphic indicative of the horizon orientation of the second viewpoint. Then, in response to the integration of the reticle overlay graphic indicative of the horizon orientation of the second viewpoint, processing facility 404 may receive user input indicating that the user selects to view imagery of the body from the second viewpoint instead of viewing the imagery of the body from the first viewpoint. In response to this user input, processing facility 404 may direct the display device to switch from displaying the imagery of the body from the first viewpoint to displaying the imagery of the body from the second viewpoint.

Figure 5:
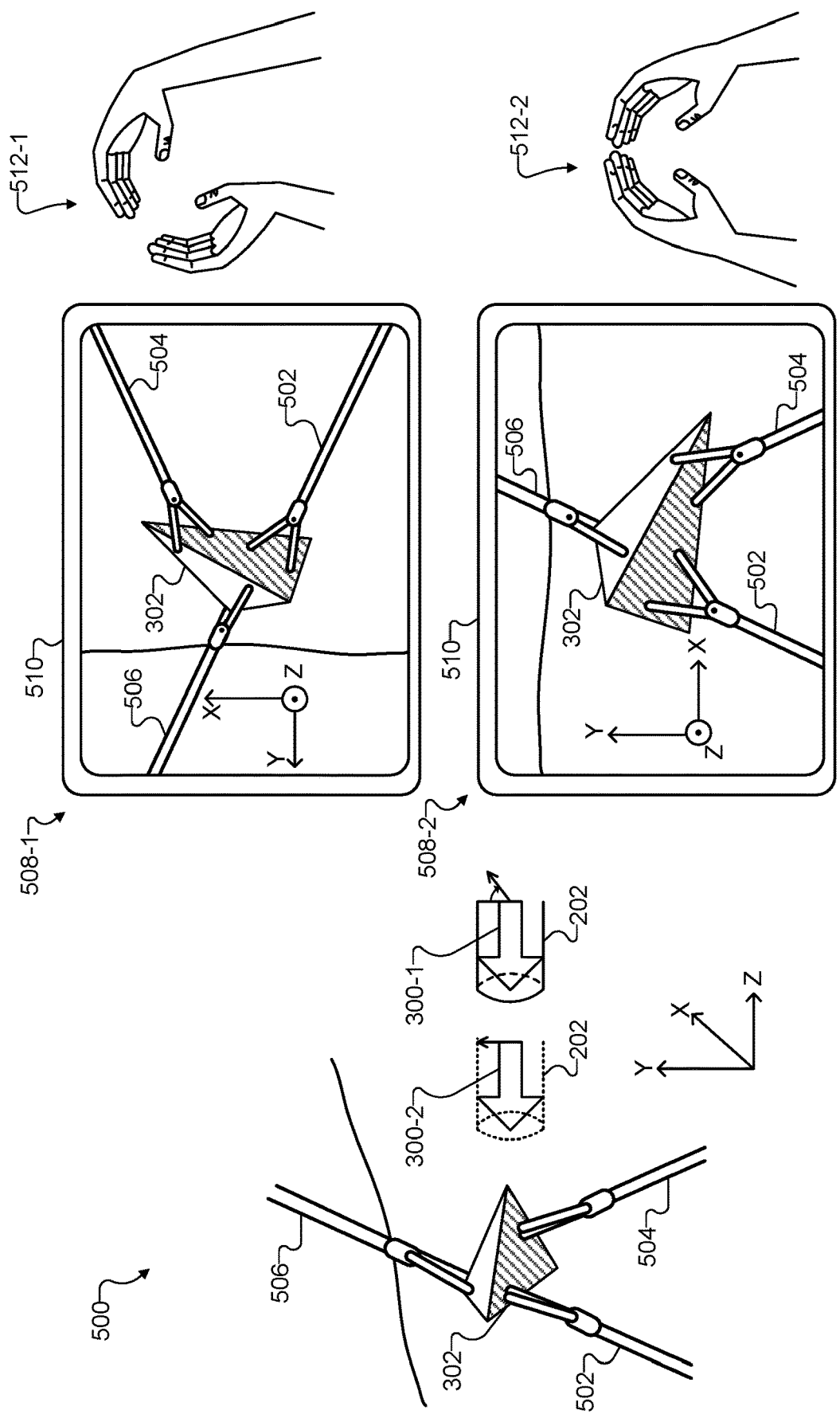
FIG. 5A illustrates an exemplary operating session during which a computer-assisted operation system performs a plurality of operations with respect to a body while an imaging device included within the computer-assisted operation system captures imagery of the body from different exemplary viewpoints according to principles described herein.
FIG. 5B illustrates an exemplary display device upon which the imagery captured from the different viewpoints during the operating session of FIG. 5A is displayed according to principles described herein.
FIG. 5C illustrates exemplary wrist postures used by the user to perform an operation while viewing imagery from the different viewpoints illustrated in FIGS. 5A and 5B according to principles described herein.

To illustrate, FIG. 5A shows an exemplary operating session 500 during which operation system 100 (or, in other examples, another computer-assisted operation system similar to operation system 100) performs a plurality of operations with respect to body 302, while imaging device 202 (which may be included within operation system 100) captures imagery of body 302 from different exemplary viewpoints 300 (e.g., viewpoints 300-1 and 300-2). More specifically, FIG. 5A depicts, from a side perspective showing the position of imaging device 202, a specific portion of body 302 where an incision has been made and a relative position of a distal end of imaging device 202 with respect to the incision. As shown, various instruments 502, 504, and 506 are being used to perform one or more operations with respect to body 302 at the operation site. For example, instruments 502 and 504 may be used primarily to manipulate tissue and/or tools in furtherance of the operations being performed, while instrument 506 may be used to hold certain portions of tissue out of the way or to otherwise facilitate the performance of the operations.

In FIG. 5A, the distal end of imaging device 202 is depicted at a first moment in time (depicted using solid lines) and at a second, later moment in time (depicted using dotted lines). As shown, imaging device 202 has a first viewpoint 300-1 at the first moment in time and a second viewpoint 300-2 at the second moment in time. A small arrow depicted at the back of each of viewpoints 300-1 and 300-2 indicates a horizon orientation (i.e., how imaging device 202 is rotated along the longitudinal axis) for that viewpoint with respect to a three-dimensional ("3D") coordinate system shown to have X, Y, and Z dimensions. More particularly, the horizon orientation of viewpoint 300-1 is shown to have the positive X dimension facing up, while the horizon orientation of viewpoint 300-2 is shown to have the positive Y dimension facing up. Along with viewpoints 300-1 and 300-2 differing in their respective horizon orientations, the zoom orientation from viewpoint 300-1 to 300-2 is also shown to be adjusted because viewpoint 300-2 is nearer to (i.e., optically zoomed in on) the tissue of body 302.

FIG. 5B illustrates an exemplary display device upon which the imagery captured from viewpoints 300-1 and 300-2 during operating session 500 is displayed. Specifically, imagery 508-1 captured by imaging device 202 from viewpoint 300-1 is displayed on a display device 510 at the first moment in time, while imagery 508-2 captured by imaging device 202 from viewpoint 300-2 is displayed on display device 510 at the second moment in time when the viewpoint of imaging device 202 has been adjusted (i.e., zoomed in and rotated 90 degrees). To help clarify what is depicted within imagery 508-1 and 508-2 and how these are different from one another, it will be noted that the same coordinate system included in FIG. 5A is also shown alongside each of imagery 508-1 and 508-2 in FIG. 5B. In both cases, the Z-dimension is illustrated by a dot notation to indicate that the z-axis is to be understood to be coming straight out of the imaging device screen (i.e., parallel with the longitudinal axis of imaging device 202 in this example). However, while the X-dimension is illustrated as facing up in imagery 508-1, the 90° adjustment to the horizon orientation from viewpoint 300-1 to viewpoint 300-2 is shown to result in the Y-dimension facing up in imagery 508-2.

In FIG. 5B, display device 510 is illustrated as a rectangular, monoscopic display screen. For example, referring again to operation system 100 described above in relation to FIG. 1, display monitor 114 of auxiliary system 106 may implement such a display device 510 in certain implementations. In the same or other implementations, it will be understood that display device 510 may additionally or alternatively be implemented by other types of display screens. For instance, display device 510 may be implemented by the stereoscopic display screens of user control system 104 that were described above as being viewed by clinician 110-1 as clinician 110-1 directs manipulating system 102 to perform operations on body 302.

As mentioned above, switching from a less optimal viewpoint to a more optimal viewpoint may provide even more benefits than the significant benefit of an improved view of the operational area where operations are being performed. For example, as mentioned, a more natural, comfortable, and efficient wrist posture may be made possible by a more optimal viewpoint when a suboptimal viewpoint is associated with a relatively unnatural, uncomfortable, or inefficient wrist posture.

To illustrate, FIG. 5C shows exemplary wrist postures 512-1 and 512-2 used by a user (e.g., clinician 110-1, etc.) to perform an operation while viewing imagery from viewpoints 300-1 and 300-2, respectively. For each of wrist postures 512-1 and 512-2, the left and rights wrists are posed (i.e., positioned, oriented, etc.) to respectively mimic the poses of instruments 502 and 504. Once operation system 100 is in the normal operating mode, instrument 502 may thus be configured to follow and be directed by the left hand and wrist of the user, while instrument 504 may be configured to follow and be directed by the right hand and wrist of the user. However, as illustrated by FIG. 5C, the wrist posture required to direct the instruments as they are posed in imagery 508-1 is significantly different from the wrist posture required to direct the instruments as posed in imagery 508-2.

Specifically, as shown, wrist posture 512-1, which is associated with viewpoint 300-1 and with instruments 502 and 504 as posed in imagery 508-1, may be a relatively awkward, uncomfortable, and inefficient wrist posture for certain tasks. For example, the left arm is awkwardly brought back with the left wrist being bent backwards to a significant degree, while the right arm is extended forward with the right wrist bending forward to a somewhat unnatural degree. While this wrist posture may be acceptable or even desirable for performing certain operations, it may be suboptimal and undesirable for performing other operations. Accordingly, system 400 may define viewpoint 300-2 and direct display device 510 to display an indication of viewpoint 300-2 by displaying imagery 508-2.

As shown, in this way, system 400 may allow the user to see the more detailed view of the operating area shown in imagery 508-2, as well as to assume a more comfortable and optimal wrist posture. Specifically, as shown, wrist posture 512-2, which is associated with viewpoint 300-2 and with instruments 502 and 504 as posed in imagery 508-2, may be a more optimal (e.g., more natural, comfortable, efficient, etc.) wrist posture for certain operations than wrist posture 512-1. Accordingly, for such operations, viewpoint 300-2 may be more optimal viewpoint 300-1.

While FIGS. 5A-5C illustrate a viewpoint adjustment that includes a change to both a horizon orientation and a zoom orientation, it will be understood that system 400 may define the second viewpoint in any suitable manner, for any suitable reason, and using any suitable orientations described herein (e.g., any of orientations 304). As one example, the second viewpoint may be defined specifically to facilitate intuitive and natural motions for movements associated with an operation being performed or an operation that is anticipated to be performed next. For instance, if an operation involves driving a needle through tissue to stitch two portions of tissue together, a more optimal viewpoint may be defined to allow the needle to be driven at an angle where the wrist and hand of the user will be able to deliver a high degree of strength and control as the operation is performed. As another example, the second viewpoint may be defined to achieve an appropriate level of zoom for a particular operation to thereby be zoomed in close enough to allow the user to utilize good depth perception of tissue and objects being operated on while also being zoomed out far enough to allow the user to view a suitable amount of context around the area being operated on.

As yet another example, system 400 may define a viewpoint that has a horizon orientation that allows for a relatively convenient switching between the user controlling one instrument and controlling another instrument. For example, if the user uses his or her right hand to alternately control instruments 504 and 506 (e.g., switching back and forth between which instrument is following the right hand), it may be inefficient or burdensome to constantly make the significant wrist posture change required to direct each of these instruments in their significantly different poses. Accordingly, system 400 may define a more optimal viewpoint to be a viewpoint that accounts for the pose of, and corresponding wrist posture needed to control, both instruments 504 and 506.

To better illustrate these and other examples of how system 400 may facilitate the performance of operations by helping optimize imaging device viewpoints, FIGS. 6-11 each illustrate display device 510 displaying imagery from a first exemplary viewpoint that is suboptimal for a particular operation, and then displaying imagery from a second exemplary viewpoint that is more optimal for the particular operation. Specifically, each of FIGS. 6-11 show the imagery from the first (suboptimal) viewpoint on a depiction of display device 510 on the left side of the figure, while showing the imagery from the second (more optimal) viewpoint on a depiction of display device 510 on the right side of the figure. Additionally, to help illustrate adjustments to horizon orientation, pitch orientation, yaw orientation, and so forth, that are made between first and second viewpoints in certain examples, each depiction of imagery in FIGS. 6-11 includes a 3D coordinate system with X, Y, and Z coordinates that will be understood to be relative to body 302 and the instruments being depicted in the imagery, and thus to remain consistent between the first and second viewpoints.

Figure 6:
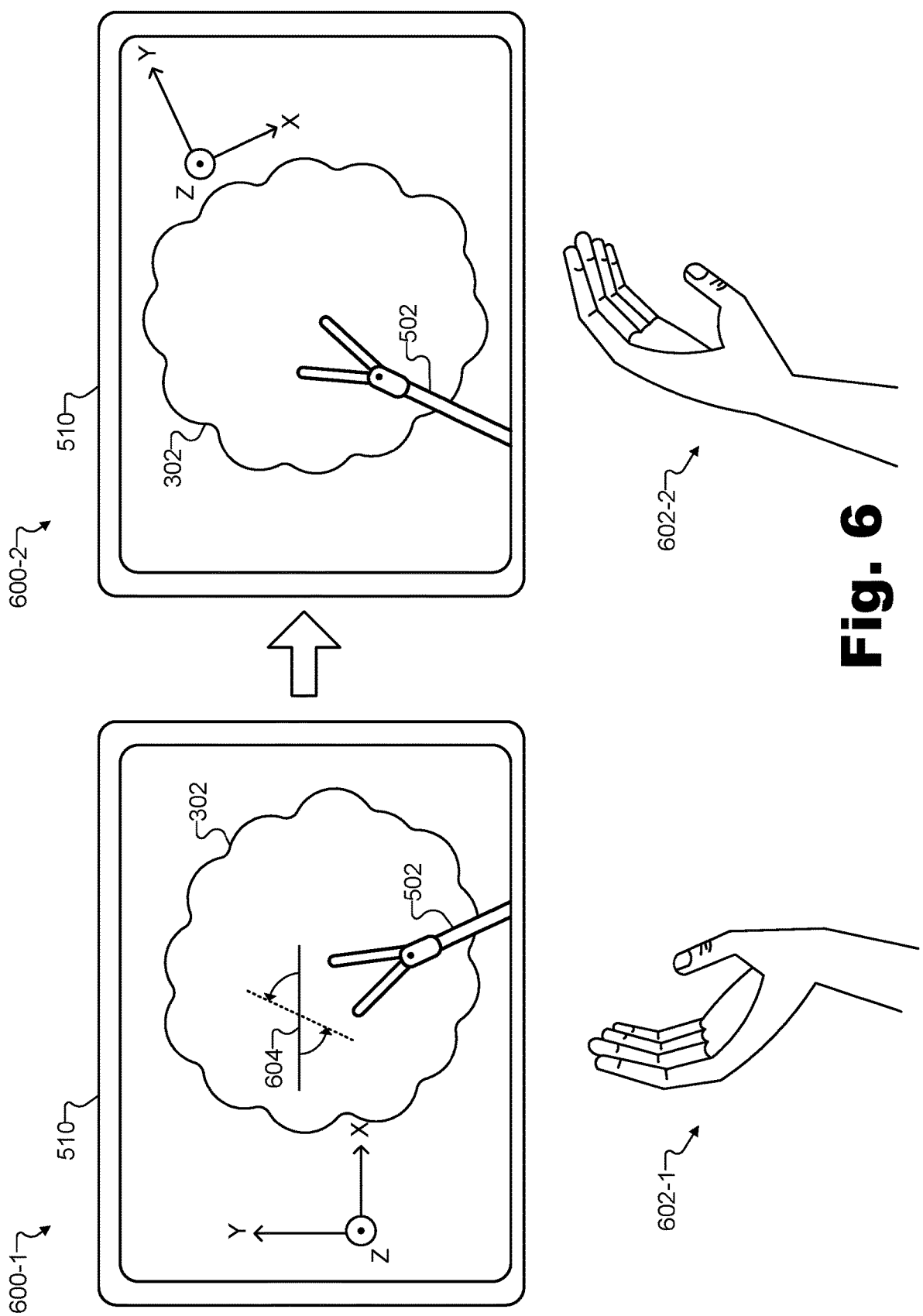
FIG. 6 illustrates a display device displaying imagery from exemplary viewpoints having different horizon orientations according to principles described herein.

FIG. 6 illustrates display device 510 displaying imagery 600-1 from a first viewpoint that will be understood to be suboptimal, and, subsequently, displaying imagery 600-2 from a second viewpoint that has a different horizon orientation than the first viewpoint and that will be understood to be more optimal than the first viewpoint. As mentioned above, system 400 may define the second viewpoint based on an identified condition associated with the operating session, and this identified condition may relate to a particular operation that is being performed (e.g., driving a needle being one exemplary operation that has been described). System 400 may determine the operation being performed or the operation that is about to be performed in any suitable way. For instance, system 400 may receive manual input from a user that indicates the operation being performed or about to be performed, or system 400 may be configured to automatically recognize the operation based on motions being performed by the user, other operations previously performed as part of a sequence, or the like.

Based on a particular operation that has been determined to be underway or forthcoming during an operating session, system 400 may analyze the user's wrist posture and define the second viewpoint accordingly. More specifically, system 400 may identify the condition associated with the operating session by, first, determining that a first wrist posture 602-1 associated with the first viewpoint is being used to direct operation system 100 to perform the particular operation, and, second, determining that a second wrist posture 602-2 associated with a viewpoint having a horizon orientation distinct from a horizon orientation of the first viewpoint would be more optimal for directing the performing of the particular operation than wrist posture 602-1. Based on identifying this condition that the user is using suboptimal wrist posture 602-1 instead of more optimal wrist posture 602-2, system 400 may define the second viewpoint based on the identified condition by defining the second viewpoint to be the viewpoint associated with wrist posture 602-2. In other words, system 400 may define the second viewpoint to be the viewpoint that would allow the user to assume more optimal wrist posture 602-2.

In other examples, system 400 may identify the condition associated with the operating session in other suitable ways or the condition may correspond to other suitable factors described herein to be associated with the operating session. For instance, in certain implementations, rather than only accounting for the current wrist posture of the user when assessing the condition of the operating session, system 400 may further account for current spatial positions of the user's hands with respect to one another, a co-location status of the user's hands with respect to instruments being controlled, or the like. In computer-assisted operation system implementations, co-orientation of the hands of a user and the instruments may be required (i.e., such that the wrist posture, finger positioning, and so forth of the hand is to be orientationally aligned with the instruments prior to instrument control by the user). However, in at least some of these implementations, co-location of the hands and the instruments may not be required (i.e., such that the hands of the user may be relatively far apart from one another in 3D space even if the instruments are relatively close to one another in 3D space, or vice versa). Accordingly, system 400 may account not only for the user's comfort and convenience in terms of wrist posture and hand orientation when determining the more optimal viewpoint, but also for comfort and convenience in terms of the spatial locations and reach of each of the hands of the user with respect to one another. In other examples, as will be described in more detail below, the identified condition may relate to specific operations being performed, the identity or known habits of the user (e.g., previously observed performance strengths and weaknesses, etc.), or any other conditions associated with the operating session as may serve a particular implementation.

Once system 400 has defined a second, more optimal viewpoint, system 400 may direct display device 510 to display an indication of the second viewpoint in any manner as may serve a particular implementation.

As one example, system 400 may direct display device 510 to display the indication of the second viewpoint by directing display device 510 to display a graphical object indicative of the second viewpoint while display device 510 is displaying imagery 600-1 of body 302 from the first viewpoint. Specifically, the graphical object may be displayed as an overlay graphic integrated with the displayed imagery of body 302 from the first viewpoint. To illustrate, FIG. 6 shows a reticle object 604 integrated with imagery 600-1 of body 302. Reticle object 604 may be one example of the types of graphical objects that may be used to indicate the second viewpoint, and additional such examples will be described and illustrated below. As shown, reticle object 604 is indicative of a horizon orientation of the second viewpoint. Specifically, in this example, a solid line representing the horizon orientation of the first viewpoint is shown together with a dotted line representative of the horizon orientation of the second viewpoint. Arrows point from the solid line to the dotted line in reticle object 604 to indicate the counterclockwise adjustment of the horizon orientation of the first viewpoint that would result in an adjustment to the second viewpoint. It will be understood that reticle object 604 is exemplary only and that, in other examples, other types or styles of reticle objects (e.g., semi-transparent crosshairs, etc.) may be used to indicate the horizon orientation of the second viewpoint as may serve a particular implementation.

In other examples, system 400 may direct display device 510 to display the indication of the second viewpoint in other ways. For example, rather than directing the display of a graphical object such as reticle object 604, system 400 may direct display device 510 to display imagery 600-2 together with imagery 600-1. For instance, system 400 may direct display device 510 to display imagery 600-2 in a picture-in-picture manner overlaying imagery 600-1, in a semitransparent manner on a different presentation layer (e.g., overlaying or underlaying the display of imagery 600-1), or in any other suitable manner. Additionally, as will be described in more detail below, system 400 may direct display device 510 to automatically or semi-automatically cease displaying imagery 600-1 and to display imagery 600-2 in place of imagery 600-1, thereby automatically adjusting imaging device 202 to capture imagery 600-2 from the second viewpoint rather than suggesting to the user how the user may manually adjust imaging device 202 to capture imagery 600-2 from the second viewpoint.

Figure 7:
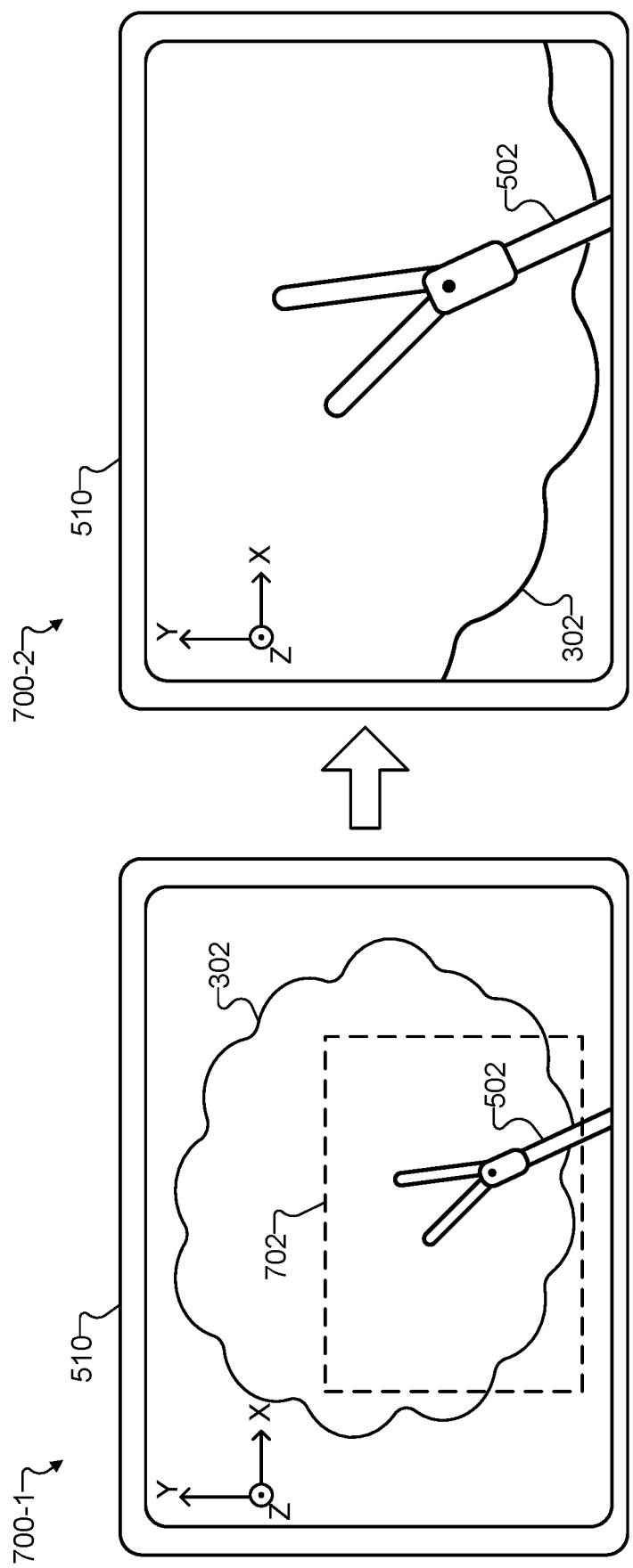
FIG. 7 illustrates a display device displaying imagery from exemplary viewpoints having different zoom orientations according to principles described herein.
Figure 8:
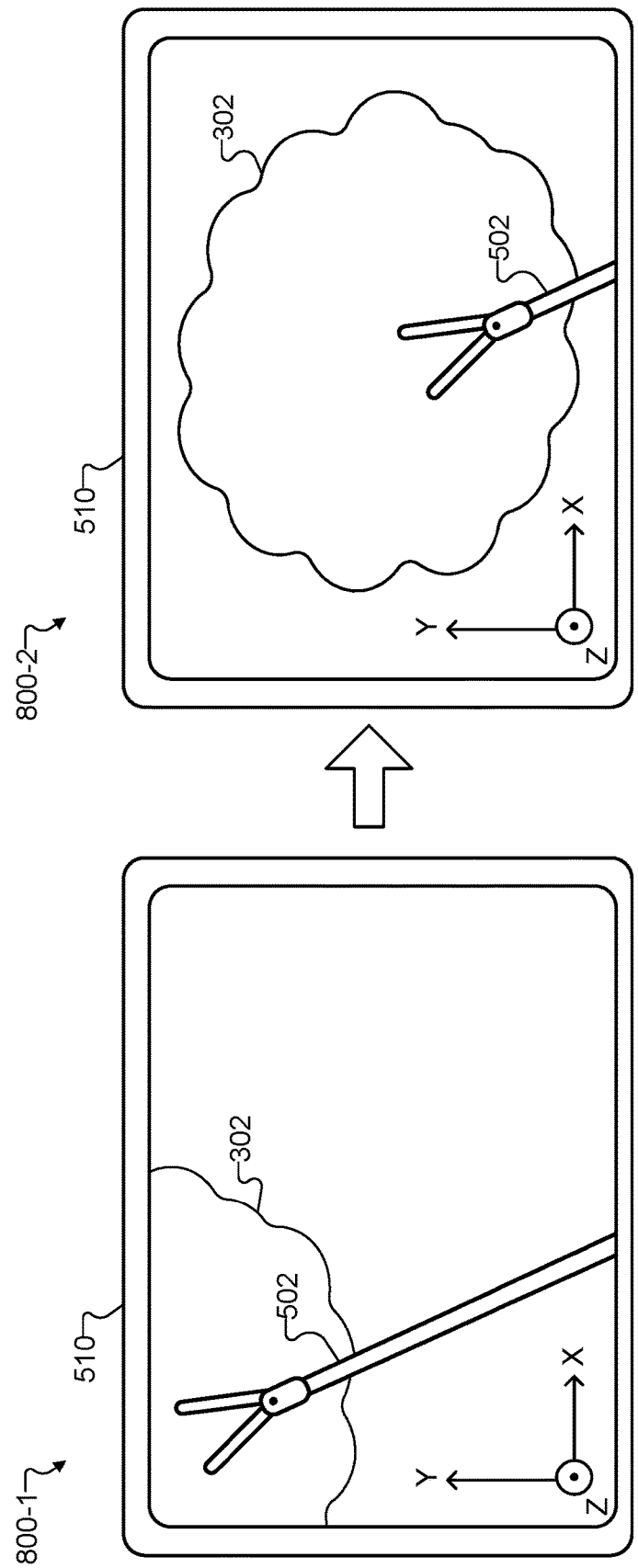
FIG. 8 illustrates a display device displaying imagery from exemplary viewpoints having different planar orientations according to principles described herein.

In addition or as an alternative to identifying a condition related to particular operations being performed and associated wrist postures for performing the operations, system 400 may identify a condition related to a pose of imaging device 202 with respect to body 302 and/or instrument 502 (and other instruments such as instruments 504 and 506 not explicitly shown in FIGS. 6-11). For example, the condition identified by system 400 and upon which the defined second viewpoint is based may be a condition relating to a relative zoom orientation of imaging device 202, a relative planar orientation of imaging device 202, or the like. FIGS. 7 and 8 each illustrate examples of optimized viewpoints defined based on these types of conditions.

Specifically, FIG. 7 illustrates display device 510 displaying imagery 700-1 from a first viewpoint that will be understood to be suboptimal, and, subsequently, displaying imagery 700-2 from a second viewpoint that has a different zoom orientation than the first viewpoint and that will be understood to be more optimal than the first viewpoint for a particular operation. In this example, system 400 may identify the condition by 1) determining that active imagery portraying a performance of the operation with respect to body 302 is depicted at a first detail level by display device 510 when displaying imagery 700-1, and 2) determining that displaying imagery of the body from a viewpoint having a zoom orientation distinct from a zoom orientation of the first viewpoint would cause the active imagery to be depicted at a second detail level more optimal for performing the operation than the first detail level. For example, system 400 may determine that the first viewpoint from which imagery 700-1 is displayed is too far zoomed out to provide an optimal level of detail, depth perception, instrument sensitivity, etc., for the particular operation being performed, and, as a result, may determine that a more optimal viewpoint would be one that has a zoom orientation that is further zoomed in to provide a greater detail level. As another example, system 400 may determine that the first viewpoint is too closely zoomed in to provide an appropriate level of context around the operation being performed and, as a result, may determine that a more optimal viewpoint would have a zoom orientation that is zoomed out to provide a lower detail level.

In either case, the defining of the second viewpoint based on the identified condition by system 400 may comprise defining the viewpoint with the more optimal zoom orientation (e.g., further zoomed in or out as the situation may call for). Specifically, system 400 may define the second viewpoint to be the viewpoint having the zoom orientation distinct from the zoom orientation of the first viewpoint so that the active imagery is depicted at the second detail level that is more optimal for performing the operation.

In the example illustrated in FIG. 7, imagery 700-1 depicts the active imagery portraying the performance of the operation with respect to body 302 at a first detail level that is relatively low. As used herein, "active imagery" portraying a performance of an operation with respect to a body refers to imagery depicting an area where the operation is being performed and where the user is focused (as opposed to other areas immediately surrounding the area of user focus). Accordingly, the active imagery at any given moment during the performance of an operation may include imagery of a portion of the body upon which the operation is being performed, as well as instruments and/or other objects being used to perform the operation, while excluding other portions of the body and/or other instruments objects not specifically related to the operation being performed.

The relatively low first detail level illustrated by imagery 700-1 may be suboptimal for performing certain operations. For example, the depth perception of the user with respect to tissue and/or objects within the active imagery may be suboptimal from a zoom orientation that is this far away from body 302 and the user may generally not be able to perceive an optimal amount of detail to perform the operation in the most efficient and effective manner. Accordingly, system 400 may define a second viewpoint where the zoom orientation is adjusted to provide a second detail level that is relatively high, such as shown in imagery 700-2. In this way, the user may enjoy visibility, depth perception, and understanding of what is happening at the operation site. Additionally, in certain examples, the instruments (e.g., instrument 502, etc.) used to perform the operation may be made more sensitive with the more detailed view, which may enable the user to more easily perform intricate movements and detailed work.

As described above in relation to FIG. 6, once system 400 defines the second viewpoint, system 400 may direct display device 510 to display an indication of the second viewpoint in various ways. As shown in FIG. 7, one manner of directing display device 510 to display the indication of the second viewpoint is to direct display device 510 to display a graphical object indicative of the second viewpoint while display device 510 is displaying imagery 700-1. Specifically, as shown, the graphical object indicative of the second viewpoint may include a bounding box 702 indicative of at least one of a zoom orientation and a planar orientation of the second viewpoint. As with reticle object 604 described above, bounding box 702 may be displayed as an overlay graphic integrated with imagery 700-1. Based on bounding box 702, a user may manually adjust the orientation parameters of imaging device 202 to move to the optimized second viewpoint and begin receiving imagery 700-2, or, in some examples, may automatically or semi-automatically adjust to the optimized viewpoint in any manner described herein.

FIG. 8 illustrates display device 510 displaying imagery 800-1 from a first viewpoint that will be understood to be suboptimal, and, subsequently, displaying imagery 800-2 from a second viewpoint that has a different planar orientation than the first viewpoint and that will be understood to be more optimal than the first viewpoint. In this example, system 400 may identify the condition by 1) determining that active imagery portraying a performance of the operation with respect to body 302 is depicted at a first part of a field of view presented by display device 510 when displaying imagery 800-1, and 2) determining that displaying imagery of the body from a viewpoint having a planar orientation distinct from a planar orientation of the first viewpoint would cause the active imagery to be depicted at a second part of the field of view more optimal for performing the operation than the first part of the field of view. For example, system 400 may determine that the first viewpoint from which imagery 800-1 is displayed shows the active imagery in a corner or side of the field of view presented by display device 510, rather than in a more optimal part of the field of view such as in the center. As a result, system 400 may determine that a more optimal viewpoint would be one that shows the active imagery in a part of the field of view that is more centered. Accordingly, the defining of the second viewpoint based on the identified condition by system 400 may comprise defining the viewpoint to move the active imagery closer to the center of the field of view. Specifically, system 400 may define the second viewpoint to be the viewpoint having the planar orientation distinct from the planar orientation of the first viewpoint so that the active imagery is depicted at the second part of the field of view that is more optimal for performing the operation.

In the example illustrated in FIG. 8, imagery 800-1 depicts the active imagery portraying the performance of the operation with respect to body 302 at a first part of the field of view of display device 510 near a corner of the field of view. Specifically, referring different parts 802-1 through 802-9 of a field of view 802 shown in a field of view key at the top of FIG. 8, the active imagery portraying the performance of the operation in imagery 800-1 is shown to be displayed largely or completely within part 802-1 of field of view 802 (i.e., in the top-left corner of the field of view). This positioning of the active imagery may be suboptimal for performing certain operations, since it may be ideal to have the active imagery near the center of the field of view (e.g., in part 802-5 or thereabouts). Accordingly, system 400 may define a second viewpoint where the planar orientation is adjusted to display the active imagery nearer the center of field of view 802, such as to be centered in part 802-5.

As described above in relation to FIGS. 6 and 7, once system 400 defines the second viewpoint, system 400 may direct display device 510 to display an indication of the second viewpoint in various ways. For example, a fully or semi-automatic change from imagery 800-1 to imagery 800-2 may be used, or an overlay graphic may be displayed to allow the user to manually adjust the parameters of imaging device 202 to reorient to the second viewpoint associated with imagery 800-2. While reticle object 604 described above in relation to FIG. 6 is highly effective in indicating a horizon orientation adjustment, and while bounding box 702 described above in relation to FIG. 7 is similarly effective for indicating a zoom orientation adjustment (possibly with a relatively minor planar orientation adjustment), these types of overlay objects may not lend themselves so effectively to the planar orientation adjustment illustrated in FIG. 8 to move from the suboptimal viewpoint of imagery 800-1 to the more optimal viewpoint of imagery 800-2. Additionally, pitch orientation adjustments, yaw orientation adjustments, and/or other orientation adjustments to imaging device 202 may similarly not be particularly well-indicated by two-dimensional overlay objects such as reticle object 604 or bounding box 702.

Accordingly, in certain examples, a graphical overlay object indicative of the second viewpoint may include a first 3D shape anchored to a field of view of imaging device 202 as imaging device 202 provides imagery of body 302 from different viewpoints, and a second 3D shape indicative of at least one of a zoom orientation, a planar orientation, a horizon orientation, a pitch orientation, and a yaw orientation of the second viewpoint. For example, while one 3D shape may appear to be anchored to imaging device 202 itself (e.g., floating in front of the imaging device as the imaging device is zoomed, panned, articulated, etc.) a target 3D shape may be anchored to body 302 such that, if the first 3D shape is matched to the target 3D shape, imaging device 202 will be adjusted to capture imagery from the second viewpoint (i.e., the more optimal target viewpoint).

Figure 9:
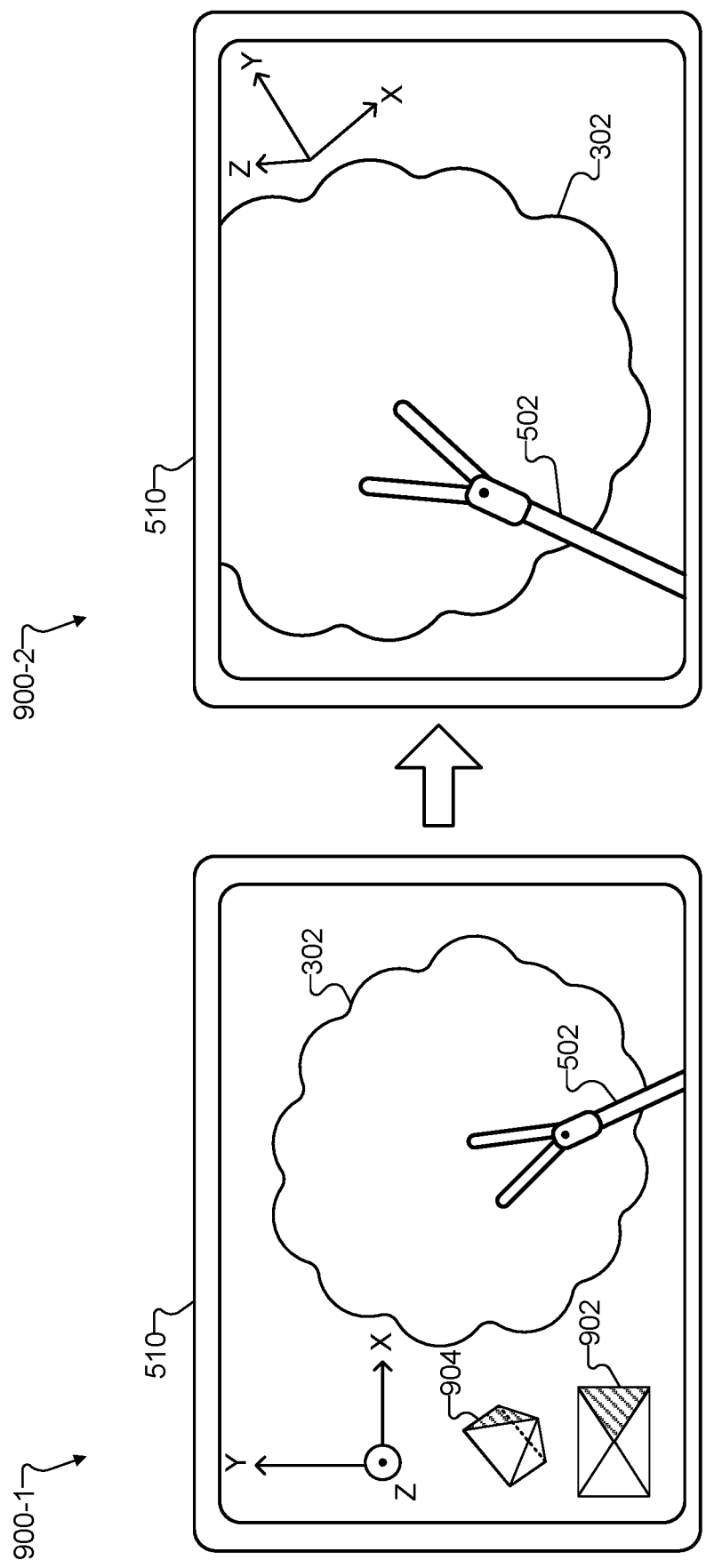
FIG. 9 illustrates a display device displaying imagery from exemplary viewpoints having orientations that are different in multiple respects according to principles described herein.

To illustrate, FIG. 9 shows display device 510 displaying imagery 900-1 from a first viewpoint that will be understood to be suboptimal, and, subsequently, displaying imagery 900-2 from a second viewpoint that has an orientation that is different in multiple respects from the orientation of the first viewpoint and that will be understood to be more optimal than the first viewpoint. As shown in FIG. 9, a first 3D shape overlay 902 is anchored to the field of view of imaging device 202 (e.g., in the bottom-left corner of the field of view in this example). In this example, 3D shape overlay 902 is a 3D pyramid shape viewed directly from the top. A face on the right-hand side of the 3D pyramid shape is shown to be shaded for illustrative clarity and orientation. Additionally, FIG. 9 shows a second 3D shape overlay 904 that is anchored to the imagery being displayed and that is indicative of the second viewpoint that has been defined. Specifically, as shown, 3D shape overlay 904 is smaller than 3D shape overlay 902 (e.g., indicating that, to align and/or match up the shapes, the zoom orientation is to be zoomed in), rotated along each of the X, Y, and Z axes with respect to 3D shape overlay 902 (e.g., indicating that, to align the shapes, the horizon orientation, pitch orientation, and yaw orientation is to be adjusted), and depicted on a different part of the field of view of display device 510 (e.g., indicating that, to align the shapes, the planar orientation is to be adjusted).

By adjusting each of the different aspects of the orientation of imaging device 202, 3D shape overlay 902 may be brought to align or match up with 3D shape overlay 904. When this alignment is achieved, imaging device 202 will be posed to capture imagery 900-2 from the second, more optimal viewpoint that system 400 defined. While each of the zoom, planar, horizon, pitch, and yaw orientations may be adjusted to move 3D shape overlay 902 to match up with 3D shape overlay 904 in this example, it will be understood that any single aspect of the orientation of imaging device 202, or any combination of these or other aspects of the orientation of imaging device 202, may be adjusted to align the 3D shape overlays in other examples.

As mentioned above, in some examples, system 400 may direct display device 510 to display the indication of the second viewpoint in ways that do not involve graphical objects overlaid onto imagery captured from the first viewpoint. For example, certain implementations of system 400 may be configured to direct display device 510 to indicate the second viewpoint by facilitating, in an automatic or semi-automatic manner, a switch from displaying the imagery from the first viewpoint to displaying the imagery from the second viewpoint. In some implementations, for instance, the directing of display device 510 to display the indication of the second viewpoint may comprise 1) directing display device 510 to present (e.g., while display device 510 is displaying the imagery of the body from the first viewpoint) an indication that the second viewpoint has been defined; 2) receiving (e.g., in response to the presenting of the indication that the second viewpoint has been defined) user input indicating that a user of the system has selected to view imagery of the body from the second viewpoint instead of viewing the imagery of the body from the first viewpoint; and 3) in response to the user input, directing display device 510 to switch from displaying the imagery of the body from the first viewpoint to displaying the imagery of the body from the second viewpoint.

Figure 10:
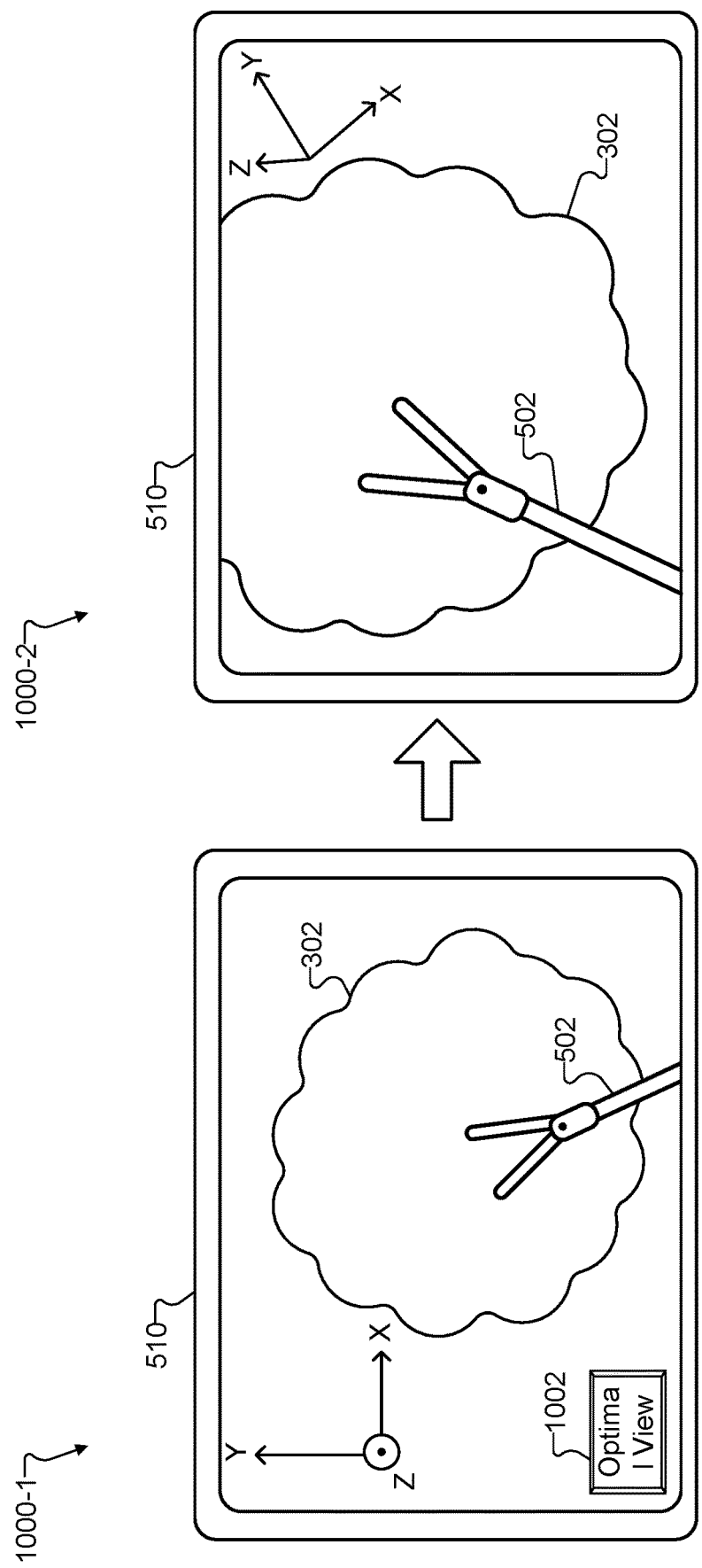
FIG. 10 illustrates a display device displaying imagery from different exemplary viewpoints that are switched between in a semi-automatic manner according to principles described herein.

To illustrate, FIG. 10 shows display device 510 displaying imagery from the same first and second viewpoints (i.e., the suboptimal first viewpoint and the second more optimal viewpoint) shown in FIG. 9 above. However, rather than facilitating a manual switch from the first viewpoint to the second viewpoint by way of graphical overlay objects such as 3D shape overlays 902 and 904, FIG. 10 illustrates an indicator 1002 indicating that system 400 has defined a second, more optimal viewpoint than the viewpoint presently in use. Indicator 1002 may take any form as may serve a particular implementation. For instance, indicator 1002 may be implemented as a button, a link, a notification, an alert, or the like. As such, the user input indicating that the user selects to view imagery of the body from the second viewpoint instead of the first viewpoint may be provided in any suitable way such as by way of a foot pedal or button press, a hand gesture, a voice command, or any other suitable form of user input. Once the user input is received, system 400 may automatically adjust orientation parameters of imaging device 202 to move to the second, more optimal viewpoint associated with imagery 1000-2. In some examples, system 400 may ensure that the viewpoint is not changed while operation system 100 is in the operating mode (i.e., the mode in which the instruments follow or mimic the user's hand movements), but, rather, is only changed while operation system 100 is in the imaging adjustment mode.

In other examples, the change from one viewpoint to another may be performed in a fully automatic manner so as to not require particular user input indicating a selection of the optimal viewpoint. In particular, it may be helpful for a novice user to get practice performing operations using the instruments of operation system 100 using automatically selected optimal viewpoints for a time before learning how to perform manual or assisted viewpoint selection as the user gets more experience with the system. In these examples, the directing of display device 510 to display the indication of the second viewpoint may comprise directing display device 510 to automatically switch, in response to the defining of the second viewpoint, from displaying the imagery of the body from the first viewpoint to displaying imagery of the body from the second viewpoint.

Figure 11:
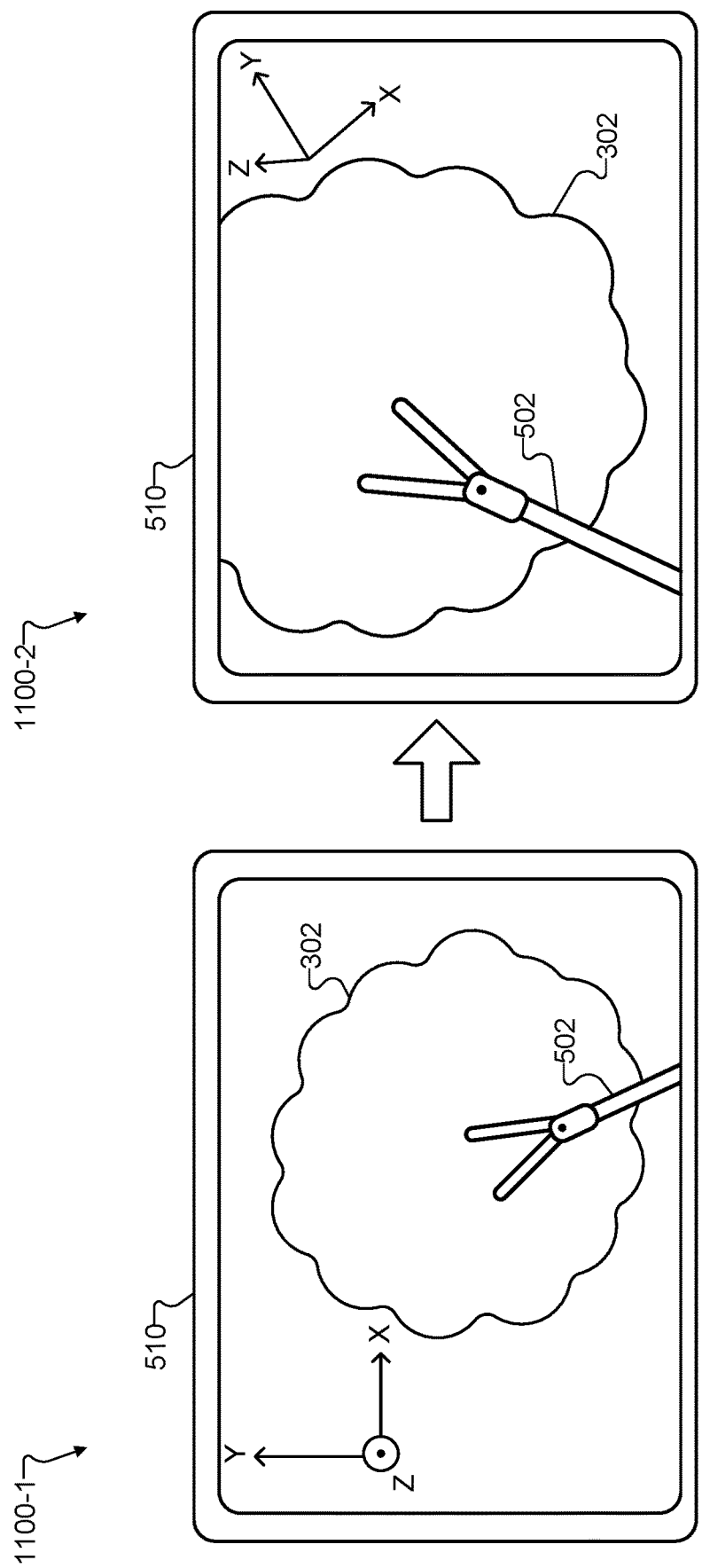
FIG. 11 illustrates a display device displaying imagery from different exemplary viewpoints that are switched between in an automatic manner according to principles described herein.

To illustrate, FIG. 11 shows display device 510 displaying imagery from the same first and second viewpoints (i.e., the suboptimal first viewpoint and the second more optimal viewpoint) shown in FIGS. 9 and 10 above. However, in the example of FIG. 11, neither an overlay object facilitating manual parameter adjustment, nor an indicator facilitating semi-automatic parameter adjustment, are included. Instead, it will be understood that system 400 may direct display device 510 to automatically switch from display imagery 1100-1 to 1100-2 once the second viewpoint is defined. In certain examples, the automatic adjustment from the first viewpoint to the second viewpoint may only be performed when operation system 100 is in the imaging adjustment mode, and not when operation system 100 is in the operating mode. For example, the user may perform an operation in the operating mode, then press a foot pedal to perform an automatic imaging adjustment, then readjust his or her wrist posture and go back into operating mode to perform the next operation in the procedure using the automatically selected viewpoint.

In other examples, system 400 may facilitate, incentivize, or encourage the user in switching to a more optimal viewpoint in other ways. For instance, if system 400 determines that a first viewpoint is highly suboptimal or that a second viewpoint is significantly more optimal than a current viewpoint, system 400 may automatically direct operation system 100 to switch from the operating mode to the imaging adjustment mode and not allow operation system 100 to switch back to operating mode until a more optimal viewpoint is selected. For example, system 400 may ensure that a particular threshold is met for one or more of the aspects of the orientation of imaging device 202 before allowing the user to continue performing operations on the body in the operating mode.

As another example, system 400 may facilitate or incentivize the use of optimized viewpoints by providing an optimization measure or optimization score for each aspect of the orientation of imaging device 202. For instance, during the performance of a particular operation, the zoom orientation may be determined to be within 10% of an optimal value while the horizon orientation may be determined to be more than 30° away from an optimal value. These measures may be used to grade users during training exercises, may be stored in a database for use later in analyzing the user's specific viewpoint selection strengths and weaknesses (as will be described in more detail below), or may be otherwise used to facilitate viewpoint optimization in any manner as may serve a particular implementation.

As yet another example, system 400 may be configured to automatically adjust a viewpoint based on a detected wrist posture, rather than the other way around, as may be done conventionally. Specifically, in certain conventional implementations, a user may select a viewpoint while operation system 100 is in the imaging adjustment mode, then, to switch to the operating mode, the user may be required to conform his or her wrist posture to that required by the selected viewpoint and to perform a hand gesture (e.g., a pinch or the like) to go into the operating mode where the instruments will follow the user's movements. In some implementations, operation system 100 may be configured to facilitate this process by physically moving the master controls that the user holds to appropriate positions for a particular viewpoint after the viewpoint has been selected. Accordingly, instead of conforming the wrist posture to a selected viewpoint in these conventional ways, certain implementations of system 400 may allow the user to select a wrist posture for one or both of his or her wrists, and then may automatically define a viewpoint that conforms fully to that wrist posture or that conforms to the wrist posture to at least some degree. Once the parameters of the imaging device are set to capture imagery from this automatically defined viewpoint, a notification may inform the user that an optimal viewpoint is available and, with a hand gesture (e.g., a pinch), the user may proceed to perform the operation in the operating mode.

In describing FIGS. 7-11, various examples have been disclosed relating to how optimized viewpoints, once defined by a viewpoint optimization system such as system 400, may facilitate the performance of certain operations. Various methods for facilitating users in switching from suboptimal to more optimal viewpoints have also been described. To achieve these ends, system 400 may be configured to define optimized viewpoints in any manner and using any information received from any source as may serve a particular implementation.

Figure 12:
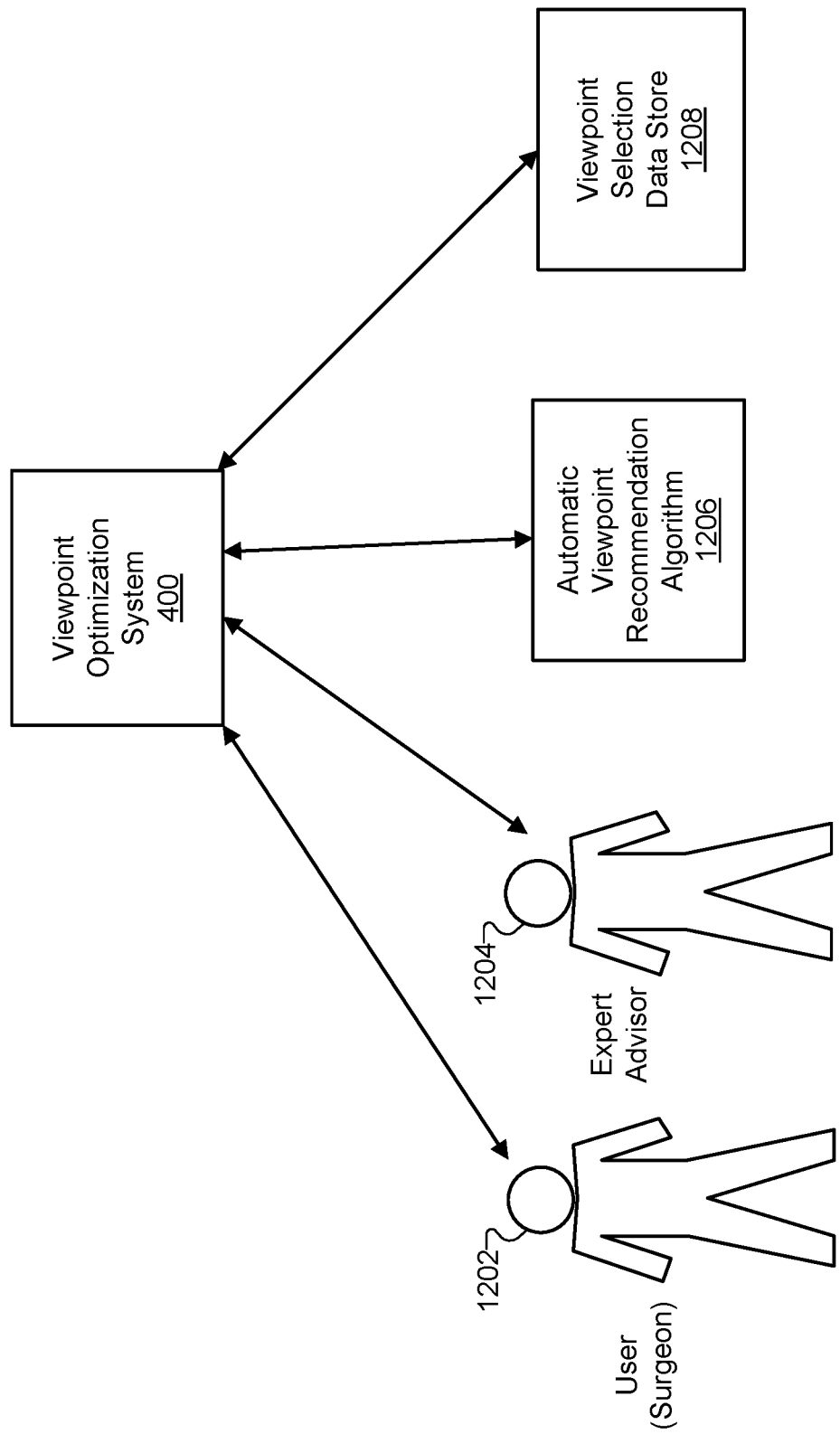
FIG. 12 illustrates exemplary entities that may provide input data to the viewpoint optimization system of FIG. 4 according to principles described herein.

To illustrate, FIG. 12 shows exemplary entities 1202 through 1208 that may provide input data to system 400 to allow system 400 to facilitate optimization of an imaging device viewpoint in the ways described herein. Specifically, as shown in FIG. 12, a user 1202, an expert advisor 1204, an automatic viewpoint recommendation algorithm 1206, and a viewpoint selection data store 1208 may each provide input to certain implementations of system 400. Each of entities 1202 through 1208 will now be described in more detail, along with various ways that these entities may provide data to system 400 to enable system 400 to define more optimized viewpoints than viewpoints that may currently be selected.

User 1202 may perform any of the actions described herein as being performed by a user. In certain examples, user 1202 may be a clinician (e.g., clinician 110-1) such as a surgeon performing a medical procedure or being trained to use operation system 100. In other examples, user 1202 may be another person on a surgical team other than the surgeon or another user of operation system 100 or another similar computer-assisted operation system.

Expert advisor 1204 may be a person distinct from user 1202 who also provides input to system 400. Expert advisor 1204 may be an experienced user of operation system 100 who is considered to have good insight into what makes one viewpoint suboptimal for a particular operation and another viewpoint more optimal for the particular operation. For example, if user 1202 is a novice surgeon being trained to use operation system 100, expert advisor 1204 may be a surgeon having more experience using operation system 100, an instructor training user 1202 on the system, or the like. In some situations (e.g., during a training session), user 1202 may operate operation system 100 and, when desiring to switch from one viewpoint to another, may put operation system 100 into a "training mode" during which user 1202 may compare his or her currently selected viewpoint with a viewpoint recommended by expert advisor 1204. To this end, the defining of the second viewpoint that is more optimal than the first viewpoint for the operation in the plurality of operations may include identifying (e.g., based on input provided in real time during the operating session by expert advisor 1204) a recommended viewpoint for the operation, and defining the second viewpoint based on the recommended viewpoint.

Automatic viewpoint recommendation algorithm 1206 may perform a similar function as expert advisor 1204, but may not require the effort of a person because it is implemented as a computer algorithm that operates on system 400, operation system 100, or on another suitable computing system. More specifically, automatic viewpoint recommendation algorithm 1206 may be configured to generate operation-specific viewpoint recommendations in real time during an operating session. In certain examples employing automatic viewpoint recommendation algorithm 1206, the defining of the second viewpoint that is more optimal than the first viewpoint for the operation in the plurality of operations may therefore include identifying (e.g., based on automatic viewpoint recommendation algorithm 1206) a recommended viewpoint for the operation and defining the second viewpoint based on the recommended viewpoint.

Viewpoint selection data store 1208 may be implemented as any suitable type of data store (e.g., a database, a data storage facility, etc.) that is configured to track and store user-specific and/or expert-specific viewpoint selection data. For example, as mentioned above, as user 1202 performs operations and corresponding viewpoint selection tasks over the course of time (e.g., over the course of a training program, over the course of his or her career, etc.), viewpoint selection data representative of effective and less effective viewpoint selection decisions made by user 1202 may be stored in viewpoint selection data store 1208. In this way, data stored in viewpoint selection data store 1208 may indicate viewpoint selection strengths and weaknesses that user 1202 is known to have. For instance, user 1202 may be known to consistently select appropriate zoom orientations but to struggle to find the right horizon orientation for certain tasks. Accordingly, in some examples, system 400 may employ data received from viewpoint selection data store to account for the fact that user 1202 (and not some other user) is performing the operating session, to account for the general skill and experience level of user 1202, to account for certain tendencies, strengths, and/or weaknesses of user 1202, and so forth. Specifically, in these examples, the identifying of the condition associated with the operating session may include determining the identity of user 1202 (i.e., the user who selected the first viewpoint) and accessing (e.g., based on the identity of user 1202) user-specific data representative of viewpoint selection performed by user 1202 in the past. System 400 may then define the second viewpoint based on the user-specific data representative of the viewpoint selection performed by user 402 in the past. In some examples, automatic viewpoint recommendation algorithm 1206 may be used in conjunction with the data received from viewpoint selection data store 1208 to define the second viewpoint.

In the same or other examples, viewpoint selection data store 1208 may also store various types of viewpoint selection data representative of viewpoints recommended by expert advisor 1204 (or other experts) for particular operations. As such, the defining of the second viewpoint that is more optimal than the first viewpoint for the operation in the plurality of operations may include accessing data representative of viewpoint selection performed in the past by expert advisor 1204 and defining the second viewpoint based on the accessed data representative of the viewpoint selection performed in the past by expert advisor 1204. System 400 may use this data (e.g., in conjunction with automatic viewpoint recommendation 1206) to determine if a presently selected viewpoint is suboptimal and if historical viewpoints used by experts would be more optimal for a particular operation being performed.

Figure 13:
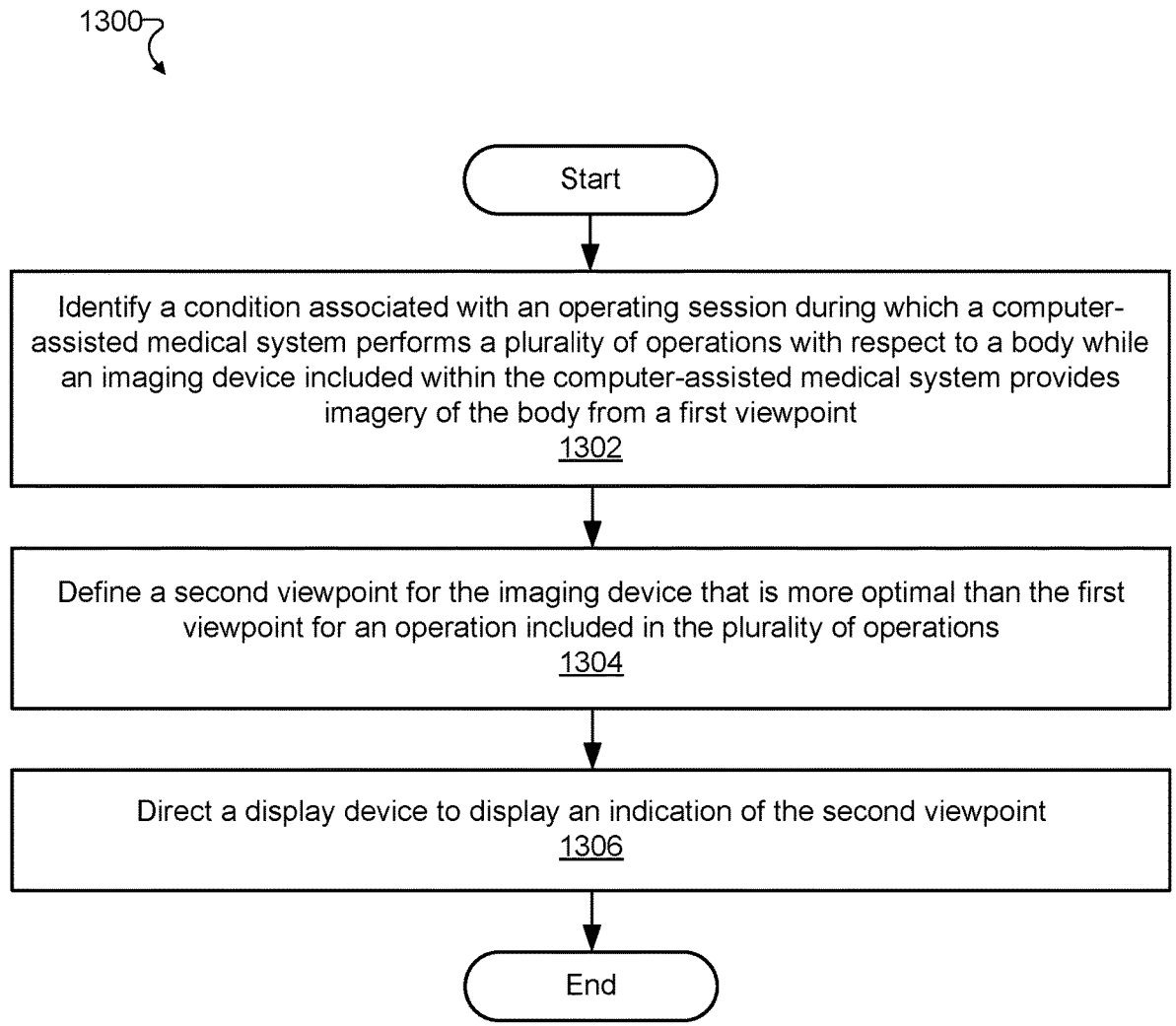
FIG. 13 illustrates an exemplary method for facilitating optimization of an imaging device viewpoint during an operating session of a computer-assisted operation system according to principles described herein.

FIG. 13 illustrates an exemplary method 1300 for facilitating optimization of an imaging device viewpoint during an operating session of a computer-assisted operation system. While FIG. 13 illustrates exemplary operations according to one embodiment, other embodiments may omit, add to, reorder, and/or modify any of the operations shown in FIG. 13. One or more of the operations shown in FIG. 13 may be performed by a viewpoint optimization system such as system 400, any components included therein, and/or any implementation thereof.

In operation 1302, a viewpoint optimization system may identify a condition associated with an operating session. In certain examples, during the operating session, a computer-assisted operation system may perform a plurality of operations with respect to a body. Additionally, during the operating session, an imaging device included within the computer-assisted operation system may provide imagery of the body from a first viewpoint. For instance, the imagery may be provided for display on a display device during the operating session. Operation 1302 may be performed in any of the ways described herein.

In operation 1304, the viewpoint optimization system may define a second viewpoint for the imaging device that is more optimal than the first viewpoint for an operation included in the plurality of operations. For example, the viewpoint optimization system may define the second viewpoint based on the condition identified in operation 1302. Operation 1304 may be performed in any of the ways described herein.

In operation 1306, the viewpoint optimization system may direct the display device to display an indication of the second viewpoint defined in operation 1304. Operation 1306 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor, etc.) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), electrically erasable programmable read-only memory ("EPROM"), FLASH-EEPROM, any other memory chip or cartridge, or any other tangible medium from which a computer can read.

Figure 14:
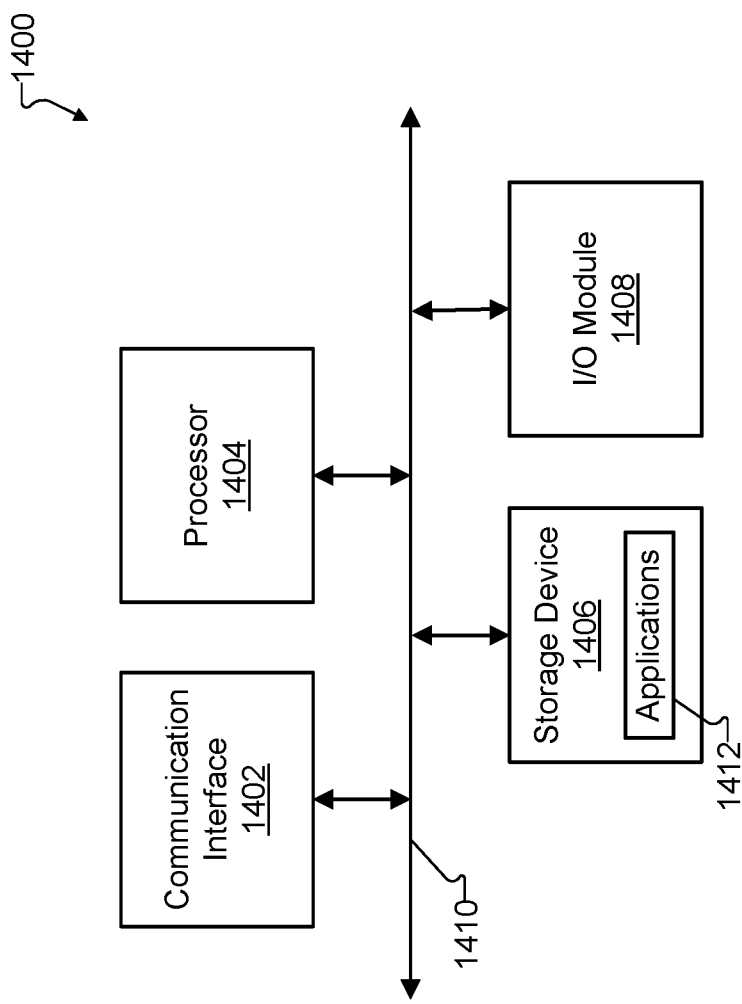
FIG. 14 illustrates an exemplary computing device according to principles described herein.

FIG. 14 illustrates an exemplary computing device 1400 that may be specifically configured to perform one or more of the processes described herein. As shown in FIG. 14, computing device 1400 may include a communication interface 1402, a processor 1404, a storage device 1406, and an input/output ("I/O") module 1408 communicatively connected via a communication infrastructure 1410. While an exemplary computing device 1400 is shown in FIG. 14, the components illustrated in FIG. 14 are not intended to be limiting. Additional or alternative components may be used in other embodiments. Components of computing device 1400 shown in FIG. 14 will now be described in additional detail.

Communication interface 1402 may be configured to communicate with one or more computing devices. Examples of communication interface 1402 include, without limitation, a wired network interface (such as a network interface card), a wireless network interface (such as a wireless network interface card), a modem, an audio/video connection, and any other suitable interface.

Processor 1404 generally represents any type or form of processing unit capable of processing data or interpreting, executing, and/or directing execution of one or more of the instructions, processes, and/or operations described herein. Processor 1404 may direct execution of operations in accordance with one or more applications 1412 or other computer-executable instructions such as may be stored in storage device 1406 or another computer-readable medium.

Storage device 1406 may include one or more data storage media, devices, or configurations and may employ any type, form, and combination of data storage media and/or device. For example, storage device 1406 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1406. For example, data representative of one or more executable applications 1412 configured to direct processor 1404 to perform any of the operations described herein may be stored within storage device 1406. In some examples, data may be arranged in one or more databases residing within storage device 1406.

I/O module 1408 may include one or more I/O modules configured to receive user input and provide user output. One or more I/O modules may be used to receive input for a single virtual reality experience. I/O module 1408 may include any hardware, firmware, software, or combination thereof supportive of input and output capabilities. For example, I/O module 1408 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1408 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1408 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1400. For example, one or more applications 1412 residing within storage device 1406 may be configured to direct processor 1404 to perform one or more processes or functions associated with processing facility 404 of system 400. Likewise, storage facility 402 of system 400 may be implemented by storage device 1406 or a component thereof.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a memory storing instructions;
a processor communicatively coupled to the memory and configured to execute the instructions to:
determine a particular operation performed during an operating session by a computer-assisted operation system, the particular operation performed with respect to a body while an imaging device included within the computer-assisted operation system provides, for display on a display device during the operating session, imagery of the body from a first viewpoint;
determine that a first wrist posture associated with the first viewpoint is being used by a user to direct the computer-assisted operation system to perform the particular operation;
determine, based on the particular operation, that a second wrist posture associated with a second viewpoint having a horizon orientation distinct from a horizon orientation of the first viewpoint would be more optimal for directing the performing of the particular operation than the first wrist posture; and
direct the display device to display an indication of the second viewpoint.

2. The system of claim 1, wherein the directing of the display device to display the indication of the second viewpoint comprises directing the display device to display a graphical object indicative of the second viewpoint while the display device is displaying the imagery of the body from the first viewpoint, the graphical object displayed as an overlay graphic integrated with the displayed imagery of the body from the first viewpoint.

3. The system of claim 2, wherein the graphical object indicative of the second viewpoint includes a reticle object indicative of a horizon orientation of the second viewpoint.

4. The system of claim 2, wherein the graphical object indicative of the second viewpoint includes a bounding box indicative of at least one of a zoom orientation and a planar orientation of the second viewpoint.

5. The system of claim 2, wherein the graphical object indicative of the second viewpoint includes:
- a first three-dimensional ("3D") shape anchored to a field of view of the imaging device as the imaging device provides imagery of the body from different viewpoints, and
- a second 3D shape indicative of at least one of a zoom orientation, a planar orientation, a horizon orientation, a pitch orientation, and a yaw orientation of the second viewpoint.

6. The system of claim 1, wherein the processor is further configured to execute the instructions to:
- receive, based on the display of the indication of the second viewpoint, user input indicating that the user has selected to view imagery of the body from the second viewpoint instead of viewing the imagery of the body from the first viewpoint; and
- direct the display device to switch, in response to the user input, from displaying the imagery of the body from the first viewpoint to displaying the imagery of the body from the second viewpoint.

7. The system of claim 1, wherein the directing of the display device to display the indication of the second viewpoint comprises directing the display device to automatically switch, based on the determining that the second wrist posture would be more optimal for directing the performing of the particular operation than the first wrist posture, from displaying the imagery of the body from the first viewpoint to displaying imagery of the body from the second viewpoint.

8. A method comprising:
- determining, by a viewpoint optimization system, a particular operation performed during an operating session by a computer-assisted operation system, the particular operation performed with respect to a body while an imaging device included within the computer-assisted operation system provides, for display on a display device during the operating session, imagery of the body from a first viewpoint;
- determining, by the viewpoint optimization system, that a first wrist posture associated with the first viewpoint is being used by a user to direct the computer-assisted operation system to perform the particular operation;
- determining, by the viewpoint optimization system based on the particular operation, that a second wrist posture associated with a second viewpoint having a horizon orientation distinct from a horizon orientation of the first viewpoint would be more optimal for directing the performing of the particular operation than the first wrist posture; and
- directing, by the viewpoint optimization system, the display device to display an indication of the second viewpoint.

9. The method of claim 8, wherein the directing of the display device to display the indication of the second viewpoint comprises directing the display device to display a graphical object indicative of the second viewpoint while the display device is displaying the imagery of the body from the first viewpoint, the graphical object displayed as an overlay graphic integrated with the displayed imagery of the body from the first viewpoint.

10. The method of claim 8, further comprising:
- receiving, based on the display of the indication of the second viewpoint, user input indicating that the user has selected to view imagery of the body from the second viewpoint instead of viewing the imagery of the body from the first viewpoint; and
- directing the display device to switch, in response to the user input, from displaying the imagery of the body from the first viewpoint to displaying the imagery of the body from the second viewpoint.

11. The method of claim 8, wherein the directing of the display device to display the indication of the second viewpoint comprises directing the display device to automatically switch, based on the determining that the second wrist posture would be more optimal for directing the performing of the particular operation than the first wrist posture, from displaying the imagery of the body from the first viewpoint to displaying imagery of the body from the second viewpoint.

12. A non-transitory computer-readable medium storing instructions that, when executed, direct a processor of a computing device to:
- determine a particular operation performed during an operating session by a computer-assisted operation system, the particular operation performed with respect to a body while an imaging device included within the computer-assisted operation system provides, for display on a display device during the operating session, imagery of the body from a first viewpoint;
- determine that a first wrist posture associated with the first viewpoint is being used by a user to direct the computer-assisted operation system to perform the particular operation;
- determine, based on the particular operation, that a second wrist posture associated with a second viewpoint having a horizon orientation distinct from a horizon orientation of the first viewpoint would be more optimal for directing the performing of the particular operation than the first wrist posture; and
- direct the display device to display an indication of the second viewpoint.

13. The non-transitory computer-readable medium of claim 12, wherein the directing of the display device to display the indication of the second viewpoint comprises directing the display device to display a graphical object indicative of the second viewpoint while the display device is displaying the imagery of the body from the first viewpoint, the graphical object displayed as an overlay graphic integrated with the displayed imagery of the body from the first viewpoint.

14. The method of claim 9, wherein the graphical object indicative of the second viewpoint includes a reticle object indicative of a horizon orientation of the second viewpoint.

15. The method of claim 9, wherein the graphical object indicative of the second viewpoint includes a bounding box indicative of at least one of a zoom orientation and a planar orientation of the second viewpoint.

16. The method of claim 9, wherein the graphical object indicative of the second viewpoint includes:
- a first three-dimensional ("3D") shape anchored to a field of view of the imaging device as the imaging device provides imagery of the body from different viewpoints, and
- a second 3D shape indicative of at least one of a zoom orientation, a planar orientation, a horizon orientation, a pitch orientation, and a yaw orientation of the second viewpoint.

17. The non-transitory computer-readable medium of claim 12, wherein the directing of the display device to display the indication of the second viewpoint comprises directing the display device to automatically switch, based on the determining that the second wrist posture would be more optimal for directing the performing of the particular operation than the first wrist posture, from displaying the imagery of the body from the first viewpoint to displaying imagery of the body from the second viewpoint.

18. The non-transitory computer-readable medium of claim 13, wherein the graphical object indicative of the second viewpoint includes a reticle object indicative of a horizon orientation of the second viewpoint.

19. The non-transitory computer-readable medium of claim 13, wherein the graphical object indicative of the second viewpoint includes a bounding box indicative of at least one of a zoom orientation and a planar orientation of the second viewpoint.

20. The non-transitory computer-readable medium of claim 13, wherein the graphical object indicative of the second viewpoint includes:
   a first three-dimensional ("3D") shape anchored to a field of view of the imaging device as the imaging device provides imagery of the body from different viewpoints, and
   a second 3D shape indicative of at least one of a zoom orientation, a planar orientation, a horizon orientation, a pitch orientation, and a yaw orientation of the second viewpoint.

* * * * *